US012268667B2

(12) United States Patent
Smith et al.

(10) Patent No.: US 12,268,667 B2
(45) Date of Patent: Apr. 8, 2025

(54) JAK1 PATHWAY INHIBITORS FOR THE TREATMENT OF PRURIGO NODULARIS

(71) Applicant: Incyte Corporation, Wilmington, DE (US)

(72) Inventors: Paul Smith, Wilmington, DE (US); Kurt Andrew Brown, Narberth, PA (US)

(73) Assignee: Incyte Corporation, Wilmington, DE (US)

(*) Notice: Subject to any disclaimer, the term of this patent is extended or adjusted under 35 U.S.C. 154(b) by 0 days.

(21) Appl. No.: 17/735,276

(22) Filed: May 3, 2022

(65) Prior Publication Data

US 2022/0378746 A1 Dec. 1, 2022

Related U.S. Application Data

(60) Provisional application No. 63/183,249, filed on May 3, 2021.

(51) Int. Cl.
*A61K 31/4155* (2006.01)
*A61K 9/00* (2006.01)
*A61K 31/437* (2006.01)
*A61K 31/497* (2006.01)
*A61K 31/519* (2006.01)
*A61K 31/5377* (2006.01)
*A61K 39/395* (2006.01)
*A61P 17/04* (2006.01)

(52) U.S. Cl.
CPC ........ *A61K 31/4155* (2013.01); *A61K 9/0053* (2013.01); *A61K 31/437* (2013.01); *A61K 31/497* (2013.01); *A61K 31/519* (2013.01); *A61K 31/5377* (2013.01); *A61K 39/3955* (2013.01); *A61P 17/04* (2018.01)

(58) Field of Classification Search
CPC .............. A61K 31/4155; A61K 9/0053; A61K 31/437; A61K 31/497; A61K 31/519; A61K 31/5377; A61K 39/3955; A61P 17/04
See application file for complete search history.

(56) References Cited

U.S. PATENT DOCUMENTS

| | | | |
|---|---|---|---|
| 5,521,184 A | 5/1996 | Zimmerman |
| 7,335,667 B2 | 2/2008 | Rodgers et al. |
| 7,598,257 B2 | 10/2009 | Rodgers et al. |
| 7,834,022 B2 | 11/2010 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,486,902 B2 | 7/2013 | Rodgers et al. |
| 8,513,270 B2 | 8/2013 | Arvanitis et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,765,734 B2 | 7/2014 | Huang et al. |
| 8,933,085 B2 | 1/2015 | Rodgers et al. |
| 8,987,443 B2 | 3/2015 | Liu et al. |
| 9,034,884 B2 | 5/2015 | Rodgers et al. |
| 9,181,271 B2 | 11/2015 | Li et al. |
| 9,193,733 B2 | 11/2015 | Rodgers et al. |
| 9,249,145 B2 | 2/2016 | Rodgers et al. |
| 9,358,229 B2 | 6/2016 | Vannucchi et al. |
| 9,359,358 B2 | 6/2016 | Rodgers et al. |
| 9,382,231 B2 | 6/2016 | Li et al. |
| 9,487,521 B2 | 11/2016 | Zhou et al. |
| 9,498,467 B2 | 11/2016 | Leopold et al. |
| 9,549,916 B2 | 1/2017 | Fu et al. |
| 9,655,854 B2 | 5/2017 | Yeleswaram et al. |
| 9,802,957 B2 | 10/2017 | Zhou et al. |
| 9,926,301 B2 | 3/2018 | Li et al. |
| 9,926,601 B2 | 3/2018 | Gertler et al. |
| 9,993,480 B2 | 6/2018 | Vannucchi et al. |
| 10,166,191 B2 | 1/2019 | Ni et al. |
| 10,435,392 B2 | 10/2019 | Li et al. |
| 11,001,571 B2 | 5/2021 | Li et al. |
| 11,103,510 B2* | 8/2021 | Montgomery ....... A61K 31/437 |
| 11,304,949 B2 | 4/2022 | Howell et al. |
| 2006/0106020 A1 | 5/2006 | Rodgers et al. |
| 2006/0183906 A1 | 8/2006 | Rodgers et al. |
| 2007/0135461 A1 | 6/2007 | Rodgers et al. |
| 2008/0312258 A1 | 12/2008 | Rodgers et al. |
| 2008/0312259 A1 | 12/2008 | Rodgers et al. |
| 2009/0233903 A1 | 9/2009 | Rodgers et al. |
| 2009/0318405 A1 | 12/2009 | Li et al. |
| 2010/0113416 A1 | 5/2010 | Friedman et al. |

(Continued)

FOREIGN PATENT DOCUMENTS

| | | |
|---|---|---|
| CN | 101910152 | 12/2010 |
| CN | 102026999 | 4/2011 |

(Continued)

OTHER PUBLICATIONS

O.E. Molloy, K. N. Bryne, B. Kirby, Successful treatment of recalcitrant nodular prurigo with tofacitinib, Jun. 2, 2020, Clinical and Experimental Dermatology (Year: 2020).*
Zeidler. Acta Derm Venereol, 2018; 98: 173-179 (Year: 2018).*
Dillon. Nature Immunology, 2004, vol. 5, No. 7 (Year: 2004).*
Reddy. Current Rheumatology Reports, 2020, 22:50 (Year: 2020).*
Ferreira, American Journal of Clinical Dermatology, 2020, 21:738-798 (Year: 2020).*
Aikawa, "Cytokine storm in the pathogenesis of multiple organ dysfunction syndrome associated with surgical insults," Nihon Geka Gakkai Zasshi, Sep. 1996, 97(9):771-777 (English abstract only).
Algre et al., "Hypothermia and hypoglycemia induced by anti-CD3 monoclonal antibody in mice: role of tumor necrosis factor," Eur. J. Immunol., 1990, 20(3):707-710.

(Continued)

Primary Examiner — Susanna Moore
Assistant Examiner — Luisalberto Gonzalez
(74) Attorney, Agent, or Firm — Fish & Richardson P.C.

(57) ABSTRACT

This disclosure relates to JAK1 pathway inhibitors and their use in treating prurigo nodularis.

20 Claims, 3 Drawing Sheets

(56) References Cited

U.S. PATENT DOCUMENTS

| | | | |
|---|---|---|---|
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0086810 A1 | 4/2011 | Rodgers et al. |
| 2011/0207754 A1 | 8/2011 | Li et al. |
| 2011/0224190 A1 | 9/2011 | Huang et al. |
| 2011/0288107 A1 | 11/2011 | Parikh et al. |
| 2012/0014968 A1 | 1/2012 | Walsh et al. |
| 2012/0149681 A1 | 6/2012 | Rodgers et al. |
| 2012/0149682 A1 | 6/2012 | Rodgers et al. |
| 2013/0018034 A1 | 1/2013 | Yao et al. |
| 2013/0045963 A1 | 2/2013 | Rodgers et al. |
| 2013/0060026 A1 | 3/2013 | Zhou et al. |
| 2014/0005166 A1 | 1/2014 | Rodgers et al. |
| 2014/0121198 A1 | 5/2014 | Li et al. |
| 2014/0135350 A1 | 5/2014 | Ni et al. |
| 2014/0256941 A1 | 9/2014 | Liu et al. |
| 2014/0343030 A1 | 11/2014 | Li et al. |
| 2015/0065447 A1 | 3/2015 | Sandor |
| 2015/0065484 A1 | 3/2015 | Yeleswaram et al. |
| 2015/0087662 A1 | 3/2015 | Li et al. |
| 2015/0118229 A1* | 4/2015 | Voss ............ A61P 27/04 514/250 |
| 2015/0246046 A1 | 9/2015 | Vaddi |
| 2015/0342952 A1 | 12/2015 | Leopold et al. |
| 2015/0344497 A1 | 12/2015 | Zhou et al. |
| 2016/0289215 A1 | 10/2016 | Li et al. |
| 2018/0162856 A1* | 6/2018 | Esteve Trias ......... A61P 3/00 |
| 2018/0312492 A1 | 11/2018 | Li et al. |
| 2019/0040043 A1* | 2/2019 | Fenster ............ A61P 17/00 |
| 2019/0175578 A1 | 6/2019 | Koblish et al. |
| 2019/0233392 A1 | 8/2019 | Wang et al. |
| 2019/0255053 A1* | 8/2019 | Montgomery ...... A61K 31/573 |
| 2019/0328739 A1 | 10/2019 | Howell et al. |
| 2019/0331697 A1 | 10/2019 | Howell et al. |
| 2020/0010456 A1 | 1/2020 | Li et al. |
| 2020/0063188 A1 | 2/2020 | Howell et al. |
| 2020/0197397 A1 | 6/2020 | Arkin et al. |
| 2021/0238168 A1 | 8/2021 | Li et al. |
| 2021/0346279 A1 | 9/2021 | Zighelboim et al. |
| 2021/0380563 A1 | 12/2021 | Zhou et al. |
| 2022/0040187 A1 | 2/2022 | Montgomery et al. |

FOREIGN PATENT DOCUMENTS

| | | |
|---|---|---|
| JP | 2013522214 | 6/2013 |
| JP | 6415543 | 10/2018 |
| WO | WO 2000009495 | 2/2000 |
| WO | WO 2000053595 | 9/2000 |
| WO | WO 2001014402 | 3/2001 |
| WO | WO 2001064655 | 9/2001 |
| WO | WO 2002000196 | 1/2002 |
| WO | WO 2003024967 | 3/2003 |
| WO | WO 2003037347 | 5/2003 |
| WO | WO 2003099771 | 12/2003 |
| WO | WO 2004005281 | 1/2004 |
| WO | WO 2004046120 | 6/2004 |
| WO | WO 2004056786 | 7/2004 |
| WO | WO 2004080980 | 9/2004 |
| WO | WO 2005028444 | 3/2005 |
| WO | WO 2006056399 | 6/2006 |
| WO | WO 2009114512 | 9/2009 |
| WO | WO 2011130146 | 10/2011 |
| WO | WO 2012068450 | 5/2012 |
| WO | WO 2012076063 | 6/2012 |
| WO | WO 2012177606 | 12/2012 |
| WO | WO 2013036611 | 3/2013 |
| WO | WO 2013040863 | 3/2013 |
| WO | WO 2014184275 | 11/2014 |
| WO | WO 2014184327 | 11/2014 |
| WO | WO 2014184328 | 11/2014 |
| WO | WO 2014184350 | 11/2014 |
| WO | WO 2017096331 | 6/2017 |
| WO | WO 2017165571 | 9/2017 |
| WO | WO 2018013918 | 1/2018 |
| WO | WO 2021076124 | 4/2020 |
| WO | WO 2020219640 | 10/2020 |

OTHER PUBLICATIONS

Argentina Office Action in Argentina Application No. 20140101971, dated Nov. 22, 2019, 6 pages.

Australian Office Action in Australian Application No. 2018223058, dated Apr. 8, 2019, 4 pages.

Australian Office Action in Australian Application No. 2018223058, Dec. 17, 2019, 4 pages.

Barabino et al., "Tear film and ocular surface tests in animal models of dry eye: uses and limitations," Experimental Eye Research, 2004, 79: 613-621.

Beck et al., "Brief Report: Alleviation of Systemic Manifestations of Castleman's Disease by Monoclonal Anti-Interleukin-6 Antibody," N. Engl. J. Med., 1994, 330(9): 602-605.

Belzberg, et al., "Prurigo Nodularis Is Characterized by Systemic and Cutaneous T Helper 22 Immune Polarization," J Invest Dermatol., 2021, 141(9):2208-2218.e14.

Bennett et al., "Proposals for the classification of the myelodysplastic syndromes," British Journal of Haematology, 1982, 51: 189-199.

Berge et al., "Pharmaceutical salts", J. Pharma. Science, 1977, 66(1): 1-19.

Bhattacharya et al., "Brittain, ed. Polymorphism in Pharmaceutical Solids," 2009, p. 327-345.

Blom et al., "Optimizing Preparative LC/MS Configurations and Methods for Parallel Synthesis Purification," J. Comb. Chem., 2003, 5: 670-683.

Blom et al., "Preparative LC-MS Purification: Improved Compound-Specific Method Optimization," J. Comb. Chem., 2004, 6: 874-883.

Blom, "Two-Pump at-Column-Dilution Configuration for Preparative Liquid Chormatography—Mass Spectrometry," J. Comb. Chem., 2002, 4: 295-301.

Bock et al. "Managing drug resistance in cancer: lessons from HIV therapy." Nature, Jul. 2012, vol. 12, pp. 494-501.

Bolen, "Nonreceptor tyrosine protein kinases", Oncogene, 1993, 8(8):2025-31.

Bollrath et al., "gp130-Meidated Stat3 Activation in Enterocytes Regulates Cell Survival and Cell-Cycle Progression during Colitis-Associated Tumorigenesis," Cancer Cell, 15: 91-102 (2009).

Borgia et al., "Features, Treatment, and Outcomes of Macrophage Activation Syndrome in Childhood-Onset Systemic Lupus Erythematosus," Arthritis Rheumatol., 2018, 70(4):616-624.

Borie et al., "Combined Use of the Jak3 Inhibitor CP-690, 550 with Mycophenolate Mofetil to Prevent Kidney Allograft Rejection in Nonhuman Primates," Transplantation, Dec. 2005, 80(12): 1756-64.

Bosworth, "JAK1/JAK2 Inhibitor Ruxolitinib Is a Rising Start," Clinical Oncology, Apr. 2011, 06:04, 3 pages.

Boudny, et al., "JAK/STAT signaling pathways and cancer", Neoplasm, 49:349-355, 2002.

Bowman, et al. "STATs in oncogenesis", Oncogene, 19:2474-2488, 2000.

Brentjens et al., "Treatment of chronic lymphocytic leukemia with genetically targeted autologous T cells: case report of an unforeseen adverse event in a phase I clinical trial," Mol Ther, 2010, 18:666-668.

Broglie et al., "Ruxolitinib for treatment of refractory hemophagocytic lymphohistiocytosis," blood advances, Aug. 22, 2017, 1(19):1533-1536.

Bromberg et al., "Inflammation and Cancer: IL-6 and STA T3 Complete the Link," Cancer Cell, 15 :79-80 (2009).

Brunning and Germing, "Myelodysplastic syndromes/neoplasms" in Chapter 5, Swerdlow, et al., eds. WHO Classification of Tumours of Haematopoietic and Lymphoid Tissues. (ed. 4th edition): Lyon, France: IARC Press, 2008, 4th edition, pp. 88-103.

Bugelski et al., "Monoclonal antibody-induced cytokine-release syndrome," Expert Review of Clinical Immunology, 2009, 5(5):499-521.

(56) References Cited

OTHER PUBLICATIONS

Burdeinick-Kerr et al., "Noncytolytic Clearance of Sindbis Virus Infection from Neurons by Gamma Interferon Is Dependent on Jak/Stat Signaling," Journal of Virology, Apr. 2009, 83(8):3429-3435.

Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.

Burger, et al., "Gp130 and ras mediated signaling in human plasma cell line IN/a-6: a cytokine-regulated tumor model for plasmacytoma", Hematol J., 2:42-53, 2001.

Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.

Candotti et al., "Molecular aspects of primary immuno-deficiencies: lessons from cytokine and other signaling pathways.", J Clin Invest, 2002, 109(10): 1261-9.

Candotti et al., "Structural and functional basis for JAK3-deficient severe combined immunodeficiency.", Blood, 1997, 90(10): 3996-4003.

Cetkovic-Cvrlje et al., "Targeting JAK3 with JANEX-1 for prevention of autoimmune type 1 diabetes in NOD mice.", Clin Immunol, 2003, 106(3): 213-25.

Chalandon, "Targeting mutated protein tyrosine kinases and their signaling pathways in hematologic malignancies", Haematologica, 2005, 90 (7):949-68.

Changelian et al., "Prevention of Organ Allograft Rejection by a Specific Janus Kinase 3 Inhibitor", Science, 2003, 302, 875-878.

Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3):333-337.

Chen et al., "Blockade of interleukin-6 signaling augments regulatory T-cell reconstitution and attenuates the severity of graft-versuslhost disease," Blood, Jul. 2009, 114(4): 891-900.

Chen et al., "Rhinovirus Induces Airway Epithelial Gene Expression through Double-Stranded RNA and IFN-Dependent Pathways," Am J of Respir Cell and Mol Bio., Feb. 2006, 34(2):192-203.

Chen et al., "Induction of myelodysplasia by myeloid-derived suppressor cells," J Clin Invest, Nov. 2013, 123(11): 4595-611.

Chen, et al., "Stat3 Activation in Human Endometrial and Cervical Cancer", British Journal of Cancer, 96, 591-599, 2007.

Cheson et al., "Report of an international working group to standardize response criteria for myelodysplastic syndromes," Blood, Dec. 2000, 96(12): 3671-4.

Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.

Cilloni et al., "Emerging drugs for chronic myeloid leukemia", Expert Opinion on Emerging Drugs, (Jun. 2010) vol. 15, No. 2, pp. 175-184.

Claessens et al., "In vitro proliferation and differentitation of erythyroid progenitors from patients with myelodysplastic syndromes: evidence for Fas-dependent apoptosis," Blood, Mar. 2012, 1594-1601.

Clark et al., "Discovery and Development of Janus Kinase (JAK) inhibitors for Inflammatory Diseases," J Med Chem., 2014, pp. A-P.

Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.

Costa Rican Office Action in Costa Rican Application No. 2015-0633, dated Feb. 25, 2020, 13 pages.

Costa Rican Office Action in Costa Rican Application No. 2015-0633, dated Sep. 20, 2019, 14 pages.

Covington et al., "Preclinical characterization of itacitinib (INCB039110), a novel selective inhibitor of JAK1 , for the treatment of inflammatory diseases," Euro J Pharmacol., Aug. 28, 2020, 885:173505.

Das et al., "Janus kinase inhibition lessens inflammation and ameliorates disease in murine models of hemophagocytic lymphohistiocytosis," Blood, Jan. 29, 2016, 127(3):1666-1675.

De Vos et al., (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haema.

Deuse, T. et al., "Novel Immunosuppression: R348, a JAK3- and Syk-Inhibitor Attenuates Acute Cardiac Allograft Rejection", Transplantation, 2008, 85(6) 885-892.

Dudley et al., "A VEGF/JAK2/STAT5 axis may partially mediate endothelial cell tolerance to hypoxia," Biochem J, Sep. 2005, 390(Pt 2): 427-36.

Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), A.

Eurasian Office Action in Eurasian Application No. 201592199, dated Feb. 4, 2019, 7 pages.

European Search Report in European Application No. 18215671.1, dated May 14, 2019, 5 pages.

Fayad et al., "Interleukin-6 and interleukin-10 levels in chronic lymphocytic leukemia: correlation with phenotypic characteristics and outcome," Blood, Jan. 2001, 97(1): 256-263.

Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.

Fenaux, et al., "Efficacy of azacitidine compared with that of conventional care regimens in the treatment of higher-risk myelodysplastic syndromes: a randomised, open-label, phase III study," Lancet Oncol, Mar. 2009, 10: 223-32.

Ferran et al., "Cytokine-related syndrome following injection of anti-CD3 monoclonal antibody: further evidence for transient in vivo T cell activation," Eur. J. Immunol., 1990, 20(3):509-515.

Ferran et al., "Inter-mouse strain differences in the in vivo anti-CD3 induced cytokine release," Clin. Exp. Immunol., 1991, 86(3):537-543.

Flex et al., "Somatically acquired JAK1 mutations in adult acute lymphoblastic leukemia," J Exp Med., 2008, 205(4):751-758.

Fonesca et al., "Interleukin-6 as a key player in systemic inflammation and joint destruction," Autoimmunity Reviews, 2009, 8(7):538-542.

Fridman et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007.

Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13.

Fridman et al., "Preclinical evaluation of local JAK1 and JAK2 inhibition in cutaneous inflammation", Journal of Investigative Dermatology, (Sep. 2011) vol. 131, No. 9, pp. 1838-1844.

Fujii et al., "Aberrant expression of serine. thereonine kinase Pim-3 in hepatocellular carcinoma development and its role in the proliferation of human hepatoma cell lines" International Journal of Cancer 114: 209-218, (2005).

Furtado, "Interleukin 2 signaling is required for CD4(+) regulatory T cell function," J Exp Med., 2002, 196(6):851-857.

Gaestel et al., "Targeting innate immunity protein kinase signalling in inflammation," Nat Rev Drug Discov., Jun. 2009, 8(6):480-99.

Gantner at al., "Concanavalin A-induced T-cell-mediated hepatic injury in mice: the role of tumor necrosis factor," Hepatology, 1995, 21(1):190-198.

Gardner et al., "Decreased Rates of Severe CRS Seen with Early Intervention Strategies for CD19 CAR-T Cell Toxicity Management," ASH 2016, Abstract #586, Dec. 5, 2016, 6 pages.

(56) References Cited

OTHER PUBLICATIONS

Goodman, et al., "IL-6 Signaling in Psoriasis Prevents Immune Suppression by Regulatory T Cells," J. Immunol., Sep. 2009, 183: 3170-3176.
Gorre et al., "Clinical Resistance to STI-571 Cancer Therapy Caused by BCR-ABL Gene Mutation or Amplification." Science, 293:876, 2001.
Gottlieb et al., "Psoriasis: Emerging Therapeutic Strategies", Nat Rev Drug Disc., 4:19-34 (2005).
Grabbe et al., "Immunoregulatory mechanisms involved in elicitation of allergic—contact hypersensitivity", Immunol Today, Jan. 1998, 19(1):37-44.
Greenberg, "The myelodysplastic syndromes" in Hoffman, et al., eds. Hematology: Basic Principles and Practice (3rd ed.), Churchill Livingston; 2000:1106-1129.
Greene, Protective Groups in Organic Synthesis, 4th ed., John Wiley & Sons: New Jersey, (2007).
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, Nov. 2003, 58(11): 1101-13.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Guschin et al., "A major role for the protein tyrosine kinase JAK1 in the JAK/STAT signal transduction pathway in response to interleukin-6," Embo J, 1995, 14(7):1421-1429.
Hardwicke et al., "GSK1070916, a potent Aurora B/C kinase inhibitor with broad antitumor activity in tissue culture cells and human tumor xenograft models", Molecular Cancer Therapeutics, 2009, 8(7):1808-1817.
Hay et al., "Kinetics and biomarkers of severe cytokine release syndrome after CD19 chimeric antigen receptor-modified T-cell therapy," Immunobio Immunother., Nov. 23, 2017, 130(21):2295-2306.
He et al., "Effectiveness of baricitinib in prurigo-type atopic dermatitis : A case report," Dermatol Ther., Feb. 26, 2021, 34(2):e14878.
Huang, "Inhibition of STAT3 activity with AG490 decreases the invasion of human pancreatic cancer cells in vitro", Cancer Sci. 97(12):1417-23 (2006).
Indian Office Action in Indian Application No. 11174/DELNP/2015, dated Nov. 19, 2019, 8 pages.
International Preliminary Report on Patentability in International Application No. PCT/US2014/038388, dated Nov. 17, 2015, 7 pages.
International Preliminary Report on Patentability in International Application No. PCT/US2019/018066, dated Aug. 18, 2020, 8 pages.
International Search Report and Written Opinion in International Application No. PCT/US2014/038388, dated Sep. 1, 2014, 9 pages.
International Search Report and Written Opinion in International Application No. PCT/US2019/018066, dated Apr. 12, 2019, 12 pages.
International Search Report and Written Opinion in International Application No. PCT/US2021/035400, dated Aug. 12, 2021, 14 pages.
International Search Report and Written Opinion in International Application No. PCT/US2022/027389, dated Jul. 20, 2022, 21 pages.
Ishizaki, et al., "Pharmacological Properties of Y-27632, a Specific Inhibitor of Rho-Associated Kinases", Molecular Pharmacology, 2000, 57, 976-983.
Itagaki, et al., "Expedient Synthesis of Potent Cannabinoid Receptor Agonist (-)-CP55,940", Organic Letters, 2005; 7(19); 4181-4183.

Jädersten et al., "Long-term outcome of treatment of anemia in MDS with erythropoietin and G-CSF," Blood, Aug. 2005, 106(3): 803-11.
James, et al., "A unique clonal JAK2 mutation leading to constitutive signalling causes polycythaemia vera", Nature, 434 (7037):1144-8 (2005).
Janes et al., "Effective and selective targeting of leukemia cells using a TORC1/2 kinase inhibitor.", Nature Medicine, 2010, 16(2):205-213.
Japanese Office Action in Japanese Application No. 2016-514126, dated Feb. 27, 2018, 5 pages (English Translation).
Japanese Office Action in Japanese Application No. 2018-187613, dated Jan. 7, 2020, 4 pages.
Japanese Office Action in Japanese Application No. 2020-543559, dated Feb. 14, 2023, 8 pages.
Jee et al., "Overview: animal models of osteopenia and osteoporosis", J Musculoskel. Neuron, Interact., 2001, 1(3):193-207.
Juvekar and Ruggeri, "Presentation: Preclinical Efficacy, PD and MoA Studies of Ruxolitinib and Itacitinib in Models of GVHD to Support their Clinical Development," Nov. 29, 2017, 36 pages.
Kaercher, "Ocular symptoms and signs in patients with ectodermal dysplasia symdromes", Grafes Arch Clin Exp Ophthalmol, 2004;495-500.
Kamb, "What's wrong with our cancer models?" Nature Reviews Drug Discovery, 2005, 4:161-165.
Kantarjian et al., "Decitabine improves patient outcomes in myelodysplastic syndromes: results of phase III randomized study," Cancer, Apr. 2006, 106(8): 1794-803.
Kato et al., "Airway Epithelial Cells Produce B Cell-Activating Factor of TNF Family by an IFN-Dependent Mechanism1," J of Immunol., Nov. 15, 2006, 177(10):7164-7172.
Kaushansky, "Lineage-Specific Hematopoietic Growth Factors", NEJM, 2006, 354:2034-45.
Kawamura et al. "Molecular cloning of L-JAK, a Janus family protein-tyrosine kinase expressed in natural killer cells and activated leukocytes.", Proc Natl Acad Sci U S A, 1994, 91(14):6374-8.
Kenderian et al., "Ruxolitinib Prevents Cytokine Release Syndrome after Car T-Cell Therapy Without Impairing the Anti-Tumor Effect in a Xenograft Model," Abstracts, Biol Blood Marrow Transplant, 2017, 23:S18-S391.
Kharas, et al., "ABL Oncogenes and Phosphoinositide 3-Kinase: Mechanism of Activation and Downstream Effectors.", Cancer Res., 65(6):2047-2053, Mar. 15, 2005.
Killedar et al., "Early pathogenic events associated with Sjogren's syndrome (SjS)-like disease of the NOD mouse using microarray analysis," Lab Invest, Dec. 2006, 86(12): 1243-1260.
Kiss, Robert, "Recent developments on JAK2 inhibitors: A patent review", Expert Opinion on Therapeutic Patents, (Apr. 2010) vol. 20, No. 4, pp. 471-495.
Kola, "Can the pharmaceutical industry reduce attrition rates?" Nature Reviews Drug Discovery, 2004, 3:711-715.
Kortylewski et al., "Regulation of the IL-23 and IL-12 balance by Stat3 signaling in the tumor microenvironment", Cancer Cell, 2009, 15:114-123.
Kruh et al., "The complete coding sequence of arg defines the Abelson subfamily of cytoplasmic tyrosine kinases.", Proc. Natl. Acad. Sci., Aug. 1990, 87:5802-5806.
Kudlacz et al. "The JAK-3 inhibitor CP-690550 is a potent antiinflammatory agent in a murine model of pulmonary eosinophilia", European Journal of Pharmacology 582 (2008) 154-161.
Kumar, "Kinase drug discovery approaches in chronic myeloproliferative disorders", Oncogene, Jun. 18, 2009, 28( 24):2305-23.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai, et al., "Mechanistic Study on the Inactivation of General Acyl-CoA Dehydrogenase by a Metabolite of Hypoglycin A", J. Am. Chem. Soc., 1991, 113: 7388-7397.

(56) References Cited

OTHER PUBLICATIONS

Larson, "Myelodysplasia: when to treat and how," Best Pract Res Clin Haematol, 2006, 19(2): 293-300.

Lee et al., "Current concepts in the diagnosis and management of cytokine release syndrome," Blood, May 29, 2014, 124(2):188-195.

Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.

Léo et al., "Identification of a monoclonal antibody specific for a murine T3 polypeptide," Proc. Natl. Acad. Sci. USA, 1987, 34:1374-1378.

Levitzki, "Tyrosine kinases as targets for cancer therapy", Eur. J. Cancer 38(suppl. 5):S11-S18 (2002).

Levy, et al. "INCB018424 A Selective Janus Kinase 1/2 Inhibitor" Presentation at the 50th American Society of Hematology Annual Meeting (ASH), Dec. 8, 2008.

Levy, et al., INCB18424 Discussion presentation at the American Society of Hematology, 49th Annual Meeting and Exposition, Atlanta, GA. Abstract #558, Dec. 10, 2007, 25 pages.

Li et al., "Pim-3, a proto-oncogene with serine/threonine kinase activity, is aberrantly expressed in human pancreatic cancer and phosphorylates Bad-mediated apoptosis in human pancreatic cell lines" Cancer Research, 2006, 66(13): 6741-7.

Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010, 30 pages.

Lin et al., "Enantioselective synthesis of Janus kinase inhibitor INCB018424 via an organocatalytic aza-Michael reaction," Organic Letters, 2009, 11(9):1999-2002.

Lin, "Constitutive Activation of JAK3/STAT3 in Colon Carcinoma Tumors and Cell Lines", Am J Pathol. 167(4):969-80 (2005).

List et al., "Efficacy of lenalidomide in myelodysplastic syndromes," N Engl J Med, Feb. 2005, 352(6): 549-57.

Lübbert, et al., "Cytogenic responses in high-risk myelodysplastic syndrome following low-dose treatment with the DNA methylation inhibitor 5-aza-2'—deoxycytidine," Br J Haematol, Aug. 2001, 114(2): 349-57.

Lube et al., "Evans Syndrome at Childhood-Onset Systemic Lupus Erythematosus Diagnosis: A Large Multicenter Study," Pediatr Blood Cancer, 2016, 63:1238-1243.

Lucet et al., "The structural basis of Janus kinas 2 inhibition by a potent and specific pan-Janus kinase inhibitor," Blood, 2006, 107(1):176-183.

Macchi, et al., "Mutations of Jak-3 gene in patients with autosomal severe combined immune deficiency (SCID)", Nature 377:65-8 (1995).

Madden et al. Comparative study of two non-invasive tear film stability techniques. Curr Eye Res, 1994; 13(4):263-9.

Madhusudan et al., "Tyrosine kinase inhibitors in cancer therapy", Clin Biochem., 2004, 37(7):618-35.

Mainstone et al., "Tear meniscus measurement in the diagnosis of dry eye", Curr Eye Res, 1996; 15:653-661.

Mancini et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.

Mascarenhas, "Primary analysis of a phase II open-label trial of CB039110, a selective JAK1 inhibitor, in patients with myelofibrosis," Haematologica. 2016, pp. 1-22 and Supplemental Data, pp. 1-7.

Maschalidi et al., "Therapeutic effect of JAK 1/2 blockade on the manifestations of hemophagocytic lymphoistiocytosis in mice," Blood, May 24, 2016, 128(1):60-71.

Maude et al., "Managing Cytokine Release Syndrome Associated With Novel T Cell-Engaging Therapies," Cancer J., 2014, 20(2):119-122.

Maxson et al., "Oncogenic CSF3R Mutations in Chronic Neutrophilic Leukemia and Atypical CML," N. Engl. J. Med., 2013, 368(19):1781-1790.

Mcinnes et al., "Comparison of baricitinib, upadacitinib, and tofacitinib mediated regulation of cytokine signaling in human leukocyte subpopulations," Arthritis Res Ther., Aug. 2, 2019, 21(1):183.

McMillan, "The systemic inflammation-based Glasgow Prognostic Score: a decade of experience in patients with cancer," Cancer Treat Rev, Aug. 2013, 39(5): 534-40.

Mesa et al., "Emerging drugs for the therapy of primary and post essential thrombocythemia, post polycythemia vera myelofibrosis", Expert Opinion on Emerging Drugs England, vol. 14, No. 3 (2009) pp. 471-479.

Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117.

Mexican Office Action in Mexican Application No. MX/a/2015/015738, dated Aug. 6, 2019, 5 pages.

Meydan et al., "Inhibition of acute lymphoblastic leukaemia by a Jak-2 inhibitor", Nature. Feb. 15, 1996;379(6566):645-8.

Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).

Minegishi, et al., "Human Tyrosine Kinase 2 Deficiency Reveals Its Requisite Roles in Multiple Cytokine Signals Involved in Innate and Acquired Immunity", Immunity 25:745-55 (2006).

Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Ep.

Miyoshi et al., "Interleukin-8 concentrations in conjunctival epithelium brush cytology samples correlate with neutrophil, eosinophil infiltration, and corneal damage", Cornea, 2001;20:743-7.

Molldrem, et al., "Antithymocyte globulin for patients with myelodysplastic syndrome," Br J Haematol, Dec. 1997, 99(3): 699-705.

Molloy et al., "Successful treatment of recalcitrant nodular prurigo with tofacitinib," Clin Exper Dermatol., Jul. 18, 2020, 45(7):918-920.

Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).

Mullighan, "JAK mutations in high-risk childhood acute lymphoblastic leukemia," Proc Natl Acad Sci USA, 2009, 106(23):9414-9418.

Mullins, et al., "Prurigo Nodularis," NLM, StatPearls Publishing, dated Sep. 14, 2021 [retrieved on Aug. 4, 2022], retrieved from URL <https://www.ncbi.nlm.nih.gov/books/NBK459204/>, 6 pages.

Mundle et al., "Evidence for Involvement of Tumor Necrosis Factor-a in Apoptotic Death of Bone Marrow Cells in Myelodysplastic Syndromes," Am J Hematol, 1999, 60:36-47.

Naka, "The paradigm of IL-6: from basic science to medicine", Arthritis Res., 2002;4 Suppl 3:S233-42.

Nakagawara, "Trk receptor tyrosine kinases: A bridge between cancer and neural development." Cancer Letters, 169:107-114, 2001.

Naqvi et al., "A potential role of ruxolitinib in leukemia", Expert Opinion on Investigational Drugs, Aug. 2011, 20(8):1159-1166.

National Cancer Institute, "FDA Approval for Ruxolitinib Phosphate", http://www.cancer.gov/cancertopics/druginfo/fda-ruxolitinibphosphate posted Nov. 18, 2011 (3 pages).

Neelapu et al., "Chimeric antigen receptor T-cell therapy—assessment and management of toxicities," Nat Rev Clin Oncol., 2018, 15(1):47-62.

Neidle, Stephen, "Cancer Drug Design and Discovery," Elsevier/Academic Press, 2008, pp. 427-431.

Neubauer et al., "Jak2 Deficiency Defines an Essential Developmental Checkpoint in Definitive Hematopoiesis", Cell, 93(3): 397-409 (1998).

Neuner, et al., "Increased IL-6 Production by Monocytes and Keratinocytes in Patients with Psoriasis," J. Invest. Dermatol, 1991, 97:27-33.

(56) References Cited

OTHER PUBLICATIONS

Nicholoff et al., "Recent Insights into the immunopathogenesis of psoriasis provide new therapeutic opportunities", J. Clin. Invest., 113; 1664-1675 (2004).

Nishimoto et al., "Improvement in Castleman's disease by humanized anti-interleukin-6 receptor antibody theraphy," Blood, 2000, 95(1):56-61.

Norman, "Selective JAK1 inhibitor and selective Tyk2 inhibitor patents," Expert Opinion, Informa Healthcare. 2012, available at: <http://informahealthcare.com/doi/pdfplus/10.1517/13543776.2012.723693>.

Oetjen et al., "Sensory Neurons Co-opt Classical Inunune Signaling Pathways to Mediate Chronic Itch," Cell, Sep. 1, 2017, 171(1):217-228.e13.

Ortmann, et al., "Janus kinases and signal transducers and activators of transcription: their roles in cytokine signaling, development and immunoregulation." Arthritis Res, 2(1): 16-32 (2000).

Ostojic et al., "Ruxolitinib for the treatment of myelofibrosis", Drugs of Today, (Nov. 2011) vol. 47, No. 11, pp. 817-827.

Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.

Pardanani A., "JAK2 inhibitor therapy in myeloproliferative disorders: rationale, preclinical studies and ongoing clinical trialsJAK2 inhibitor therapy in MPD", Leukemia 22, Jan. 23-30, 2008.

Parganas et al., "Jak2 is Essential for Signaling through a Variety of Cytokine Receptors", (1998). Cell, 93(3): 385-95.

Park et al., "CP-690550, a Janus Kinase Inhibitor, Suppresses CD4 T-Cell-Mediated Acute Graft-Versus-Host Disease by Inhibiting the Interferon-y Pathway,"Transplantation, 2010, 90(8):825-835.

Park et al., "Homogeneous Proximity Tyrosine Kinase Assays: Scintillation Proximity Assay versus Homogeneous Time-Resolved Fluorescence", Analytical Biochemistry, 1999, 269: 94-104.

Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Of.

Pedranzini et al., "Pyridone 6, a pan-Janus-activated kinase inhibitor, induces growth inhibition of multiple myeloma cells," Cancer Res., 2006, 66(19):9714-9721.

Peng et al., "Tofacitinib for Prurigo Nodularis: A Case Report," Clin Cosmet Investig Dermatol., Mar. 1, 2022, 15:503-506.

Pernis et al., "JAK-STAT signaling in asthma." J Clin Invest, 2002, 109(10): 1279-83.

Peruvian Office Action in Peruvian Application No. 2406-2015, dated Sep. 26, 2019, 17 pages.

Ravin, "Preformulation", Remington's Pharmaceutical Sciences, 17th ed., Mack Publishing Company, Easton, Pa., 1985, Chapter 76, 1409-1423.

Raza et al., "Novel insights into the biology of myelodysplastic syndromes: excessive apoptosis and the role of cytokines," Int J Hematol, Jun. 1996, 63(4): 265-78.

Raza et al., "The myelodysplastic syndromes in 1996: complex stem cell disorders confounded by dual actions of cytokines," Leuk Res, Nov.-Dec. 1996, 20(11-12): 881-90.

Raza et al., "Apoptosis in bone marrow biopsy samples involving stromal and hematopoietic cells in 50 patients with myelodysplastic syndromes," Blood, Jul. 1995, 86(1): 268-76.

Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.

Remington's Pharmaceutical Sciences, 17th ed., Mack Publishing Company, Easton, Pa., 1985, p. 1418.

Reszke et al., "Emerging Therapeutic Options for Chronic Pruritus," Am J Clin Dermatol., Jun. 30, 2020, 21(5):601-618.

Roberts et al., "Trends in the risks and benefits to patients with cancer participating in phase 1 clinical trials," JAMA, Nov. 2004, 292(17): 2130-40.

Roche, "Bioreversible Carriers in Drug Design," American Pharmaceutical Association and Pergamon Press, 1987, Front Matter Only, 4 pages.

Rodig et al., "Disruption of the Jak1 gene demonstrates obligatory and nonredundant roles of the Jaks in cytokine-induced biologic responses." Cell, 93(3): 373-83 (1998).

Roudebush et al., "Pharmacologic manipulation of a four day murine delayed type hypersensitivity model," Agents Actions, Jan. 1993, 38(1-2): 116-21.

Rousvoal et al. "Janus kinase 3 inhibition with CP-690,550 prevents allograft vasculopathy", Transpl Int., 2006 19(12):1014-21.

Samanta et al., "Janus kinase 2: a critical target in chronic myelogenous leukemia", Cancer Res. Jul. 1, 2006;66(13):6468-72.

Schiffer, "Clinical issues in the management of patients with myelodysplasia," Hematology Am Soc Hematol Educ Program, 2006: 205-10.

Schiffer, "Myelodysplasia: the good, the fair and the ugly," Best Pract Res Clin Haematol, Mar. 2007, 20(1): 49-55.

Schindler et al., "Hormones and Signaling: Cytokines and STAT Signaling", Adv Pharmacol. 2000; 47:113-74.

Schrader et al., "Animal models of dry eye," Dev Opthalmol, 2008, 41:298-312.

Schram et al., "How I treat hemophagocytic lymphohistiocytosis in the adult patient ," Blood, 2005, 125(19):2908-2914.

Science IP Search Report, Mar. 2021, 421 pages.

Scott et al., "Jaks, STATs, Cytokines, and Sepsis." Clin Diagn Lab Immunol, 9(6): 1153-9 (2002).

Search Report ID SR-20210895.01, "Single Crystal Structure Determination of INCB054707 Phosphate," dated May 20, 2021, 42 pages.

Seki, "STAT3 and MAPK in human lung cancer tissues and suppression of oncogenic growth by JAB and dominant negative STAT3", Int J Oncol. 24(4):931-4 (2004).

Seto et al., "Enhanced Th2 cell-mediated allergic inflammation in Tyk2-deficient mice." J Immunol, 2003, 170(2): 1077-83.

Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.

Shi et al., "The pharmacokinetics, pharmacodynamics, and safety of orally dosed INCB018424 phosphate in healthy volunteers", Journal of Clinical Pharmacology, Dec. 2011, 51(12):1644-1654.

Shimizu et al., "Distinct cytokine profile in juvenile systemic lupus erythematosus-associated macrophage activation syndrome,"Clin Immunol., Feb. 2013, 146(2):73-76.

Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.

Silverman et al., "Randomized controlled trial of azacitidine in patients with the myelodysplastic syndrome: a study of the cancer and leukemia group B," J Clin Oncol, May 2002, 20(10): 2429-40.

Simon et al., "Therapeutic strategies for eosinophilic dermatoses," Curr Opin in Pharmacol., Feb. 10, 2019, 46:29-33.

Sloand et al., "Factors affecting response and survival in patients with myelodysplasia treated with immunosuppressive therapy," J Clin Oncol, May 2008, 26(15): 2505-11.

Smith et al., "Basic pathogenic mechanisms operating in experimental models of acute anteriior uveitis," Immunol Cell Biol, Dec. 1998, 76(6): 497-512.

Smolen et al., "Effect of interleukin-6 receptor inhibition with tocilizumab in patients with rheumatoid arthritis (Option study): a double-blind, placebo-controlled, randomised trial," Lancet, 2008, 371:987-997.

Snodgrass et al., "Cytokine Release Syndrome: CD19-directed CAR T cell therapy, Bispecifics & Haploidentical HSCT," Nov. 22, 2017, 33 pages.

Sonbol et al., "Comprehensive review of JAK inhibitors in myeloproliferative neoplasms," Therapeutic Advances in Hematology, 2013, 4(1): 15-35.

(56) References Cited

OTHER PUBLICATIONS

Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," Blood, Jun. 2014, 123(24): 3832-42.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol Chem, May 2004, 279(19):19936-47.
Staerk et. al., "JAK1 and Tyk2 activation by the homologous polycythemia vera JAK2 V617F mutation: cross-talk with IGF1 receptor", J Biol Chem., 2005, 280:41893-41899.
Ständer, et al., "Trial of Nemolizumab in Moderate-to-Severe Prurigo Nodularis," N Engl J Med., 2020, 382(8):706-716.
Stirewalt et al., "Predictors of relapse and overall survival in Philadelphia chromosome-positive acute lymphoblastic leukemia after transplantation", Biol Blood Marrow Transplant. Mar. 2003;9(3):206-12.
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Symington et al., "The relationship of serum IL-6 levels to acute graft-versus-host disease and hepatorenal disease after human bone marrow transplantation," Transplantation, Sep. 1992, 54(3): 457-62.
Takemoto et al., "Proliferation of adult T cell leukemia/lymphoma cells is associated with the constitutive activation of JAK/STAT proteins." Proc Natl Acad Sci U S A, 1997, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Taylor et al., "The JAK1-Selective Inhibitor Filgotinib Displays an Anti-Inflammatory Biomarker Signature in Rheumatoid Arthritis Patients," 2016 ACR/ARHP Annual Meeting, Abstract No. 2616, Sep. 28, 2016.
Teachey et al., "Identification of Predictive Biomarkers for Cytokine Release Syndrome after Chimeric Antigen Receptor T cell Therapy for Acute Lymphoblastic Leukemia," Cancer Discov. 6, 664-679 (2016).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Tisoncik et al., "Into the Eye of the Cytokine Storm," Microbiology and Molecular Biology Reviews, Mar. 2012, 76(1):16-32.
Toyonaga, "Blockade of constitutively activated Janus kinase/signal transducer and activator of transcription-3 pathway inhibits growth of human pancreatic cancer", Cancer Lett. 201(1):107-16 (2003).
Trikha et al., "Targeted anti-interleukin-6 monoclonal antibody therapy for cancer: a review of the rationale and clinical evidence," Clinical Cancer Research, 2003, 9: 4653-4665.
Tsoi et al., "Transcriptomic characterization of prurigo nodularis and the therapeutic response to nemolizumab," J Allergy Clin Immunol., 2022, 149:1329-1339.
Vanhoutte, "Selective JAK1 Inhibition in the Treatment of Rheumatoid Arthritis: Proof of Concept with GLPG0634, "Arthritis Rheum 64.10 (2012): S1051-1.
Vannucchi et al., "The mTOR Inhibitor, RAD001, Inhibits the Growth of Cells From Patients with Myeloproliferative Neoplasms", Blood: ASH Annual Meeting Absracts, 51st Annual Meeting of the American Society of Hematology, 2009, 114(22) , 2 pages.
Vardiman et al., "The 2008 revision of the World Health Organization (WHO) classification of myeloid neoplasms and acute leukemia: rationale and important changes," Blood, Jul. 2009, 114(5): 937-51.
Vardiman et al., "The World Health Organization (WHO) classification of the myeloid neoplasms," Blood, Oct. 2002, 100(7): 2292-302.
Verma et al., "Jak family of kinases in cancer", Cancer and Metastasis Reviews, 2003, 22(4):423-434.
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Vietnamese Office Action in Vietnamese Application No. 11-2019-01578, dated Apr. 26, 2019, 2 pages.
Winyard and Willoughby, "Methods in Molecular Biology Inflammation Protocols," Humana Press, 2003, vol. 225, 359 pages.
Wong et al., "IL-17A Induces Endothelin-1 Expression through p38 Pathway in Prurigo Nodularis," J Investigative Dermatology, 2020, 140(3):702-706.e2.
www.quora.com, "What is a 'cytokine storm,' and what are the diseases that cause that?", retrieved on Feb. 18, 2018, retrieved from URL <https://www.quora.com/What-is-a-cytokine-storm-and-what-are-the-diseases-that-cause-that>, 9 pages.
Xiaoyang et al., "Knockdown of STAT3 Expression by RNA Interference Inhibits the Induction of Breast Tumors in Immunocompetent Mice", Cancer Res Apr. 1, 2005 65; 2532.
Xie, et al., "Inflammatory mediators causing cutaneous chronic itch in some diseases via transient receptor potential channel subfamily V member 1 and subfamily A member 1," J Dermatol., 2019, 46(3):177-185.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Xu et al., "Cytokine release syndrome in cancer Immunotherapy with chimeric antigen receptor engineered T cells," Cancer Lett., 2014, 343(2):172-178.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, (Nov. 2011) vol. 7, No. 4, pp. 306-312.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, 58(11):3485-3497.
Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6):1674-1686.
Yin et al., "Successful treatment of refractory prurigo nodularis with baricitinib," Dermatol Ther., Jun. 26, 2022, e15642.
Yongjun et al., "Advances in research of tyrosine kinases inhibitor of vascular endothelial growth factor receptor," Chinese J New Drugs, Dec. 31, 2008, 17(7):544-550.
Coligan et al., "Current Protocols in Immunology," Wiley Press, Sep. 1992, vol. 3, 21 pages (Chapter Abstracts Only).
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American, Dec. 2010.
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA, Nov. 2007, 1 page.

(56) References Cited

OTHER PUBLICATIONS

Fridman et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, Nov. 2007, 1 page.

Fridman et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting, Nov. 2007, 1 page.

Harigai et al., "Selectivity of Janus Kinase Inhibitors in Rheumatoid Arthritis and Other Immune-Mediated Inflammatory Diseases: Is Expectation the Root of all Headache?," Drugs, Jul. 2020, 80(12): 1183-1201.

International Preliminary Report on Patentability in International Application No. PCT/US2022/027389, mailed on Oct. 24, 2023, 12 pages.

Lemp, "The Definition and Classification of Dry Eye Disease: Report of the Definition and Classification Subcommittee of the International Eye Workshop," The Ocular Surface, Apr. 2007, 5(2): 75-92.

Lübbert, et al., Low-dose decitabine versus best supportive care in elderly patients with intermediate- or high-risk myelodysplastic syndrome (MDS) ineligible for intensive chemotherapy: final results of the randomized phase III study of the European Org, May 2011, 10 pages.

Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 2008, 19 pages.

Punwani et al., "Efficacy and safety of topical INCB018424, a selective Janus kinase 1 & 2 (JAK1&2) inhibitor in psoriasis," Journal of the American Academy of Dermatology, Mar. 2009, vol. 60. No. 3.

Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 2008, 15 pages.

Tefferi et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 2008.

Vannucchi et al., "Inhibitorsof PI3K/Akt and/or mTOR Inhibit the Growth of Cells of Myeloproliferative Neoplasms and Synergize with JAK2 Inhibitor and Interferon", Blood, Annual Meeting Abstract 3835 A, Nov. 2011, 118(21):1638-1639.

Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abs, Nov. 2009, 2 pages.

Verstovsek, S. et al., "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 2008 (19 pages).

Verstovsek, S. et al., "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark, 2 pages.

Verstovsek, S. et al., INCB18424, an Oral, Selective JAK2 Inhibitor, Shows Significant Clinical Activity in a Phase I/II Study in Patient with Primary Myelofibrosis (PMF) and Post Polycythemia Vera/ Essential Thrombocythemia Myelofibrosis (Post-PV/ET MF), presentation at the American Society of Hematology 49th Annual Meeting and Exposition, Dec. 10, 2007 (16 pages).

Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor," INCB018424, 50th ASH Annual Meeting and Exposition, Abstract No. 2802 (2008), 18 pages.

Wagh et al., "Polymers used in ocular dosage form and drug delivery systems," Asian J. Pharma, Jan. 12-17, 2008.

Incyte.com [online], "Incyte Presents New Late-Breaking Data From Phase 2 Study Evaluating Povorcitinib In Patients With Prurigo Nodularis," Mar. 2024, retirved on Jun. 24, 2024, retrieved from <https://investor.incyte.com/news-releases/news-release-details/incyte-presents-new-late-breaking-data-phase-2-study-evaluating>, 2 pages.

Elmariah et al., "Practical approaches for diagnosis and management of prurigo nodularis: United States expert panel consensus." Journal of the American Academy of Dermatology, Mar. 2021, 84(3):747-760.

Eurasian Office Action in Eurasian Application No. 202393074, dated Oct. 14, 2024, 11 pages (with English Translation).

Kowalski et al., "Treatment-resistant prurigo nodularis: challenges and solutions," Clinical, cosmetic and investigational dermatology. Feb. 2019, 163-172.

Kwatra, "Breaking the itch-scratch cycle in prurigo nodularis," New England Journal of Medicine, Feb. 2020, 382(8):757-758.

Rambhia et al., "Recalcitrant prurigo nodularis treated successfully with dupilumab," JAAD case reports, May 2019, 5(5):471-473.

Ukranian Office Action in Ukranian Application No. a202305785, dated Oct. 1, 2024, 8 pages (with English Translation).

Harris et al., "World Health Organization classification of neoplastic diseases of the hematopoietic and lymphoid tissues: report of the Clinical Advisory Committee meeting-Airlie House, Virginia, Nov. 1997," J Clin Oncol, Dec. 1999, 17(12): 3835-3849.

Liu et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009; 15(22) pp. 6891-6900; Nov. 15, 2009; Published Online First on Nov. 3, 2009 as 10.1158/1078-0432.CCR-09-1298.

Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957.

Williams et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.

Yang et al., "Constitutive NF-KB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.

\* cited by examiner

JAK1 PATHWAY INHIBITORS FOR THE TREATMENT OF PRURIGO NODULARIS

The present application claims the benefit of U.S. Provisional Application No. 63/183,249, filed May 3, 2021, which is incorporated herein by reference in its entirety.

U.S. Provisional Application No. 63/183,225, filed May 3, 2021, and the U.S. non-provisional application entitled "Ruxolitinib for the Treatment Of Prurigo Nodularis", filed May 3, 2022, claiming priority to said U.S. Provisional Application No. 63/183,225, are incorporated herein by reference in their entireties.

TECHNICAL FIELD

This disclosure relates to JAK1 pathway inhibitors and the use thereof in treating prurigo nodularis.

BACKGROUND

Prurigo nodularis (PN) is a chronic skin disorder characterized by firm, dome-shaped, intensely pruritic nodules ranging in size from a few millimeters to several centimeters. The nodules are often symmetrically distributed on the extensor surfaces of the arms and legs and on the trunk. PN has an estimated prevalence of 72 per 100,000 persons in the US, based on people with health insurance. Reports vary on whether it more frequently in women versus men or occurs equally in men and women. People with darker or greater degrees of pigmentation in their skin are substantially more likely to have PN than patients with lighter or less pigmentation in their skin. In particular, one study found that African American patients were 3.4 times more likely to have PN than Caucasian patients.

Quality of life can be substantially negatively impacted by PN. In particular, quality of life issues include sleep disturbance, impact on job performance, and avoidance of social activities. In addition, the burden of systemic comorbidities in prurigo nodularis often exceeds that of other inflammatory skin disorders (e.g., atopic dermatitis or psoriasis). Prurigo nodularis is associated with increased rates of mental health (specifically anxiety and depression), endocrine, cardiovascular, and renal disorders, as well as HIV and malignancy. Approximately half of all patients with PN report a history of atopic dermatitis.

Pharmacologic therapy with first-generation sedating antihistamines (e.g., hydroxyzine, diphenhydramine) administered at bedtime may be useful in controlling nocturnal pruritus. Both selective serotonin reuptake inhibitors and tricyclic antidepressants are also employed for chronic pruritus, especially when a component of depression is present.

Super-potent topical corticosteroids are considered first-line therapy. Patients with widespread disease may be given phototherapy. Patients with recalcitrant PN may be given systemic treatments including systemic immunosuppressants, thalidomide, lenalidomide, and anticonvulsants. These treatments are associated with potential significant toxicity, and their efficacy in patients with recalcitrant PN has not been established. Accordingly, there is a need to develop new therapies for the treatment of prurigo nodularis. This application addresses this need and others.

SUMMARY

Figure 1:
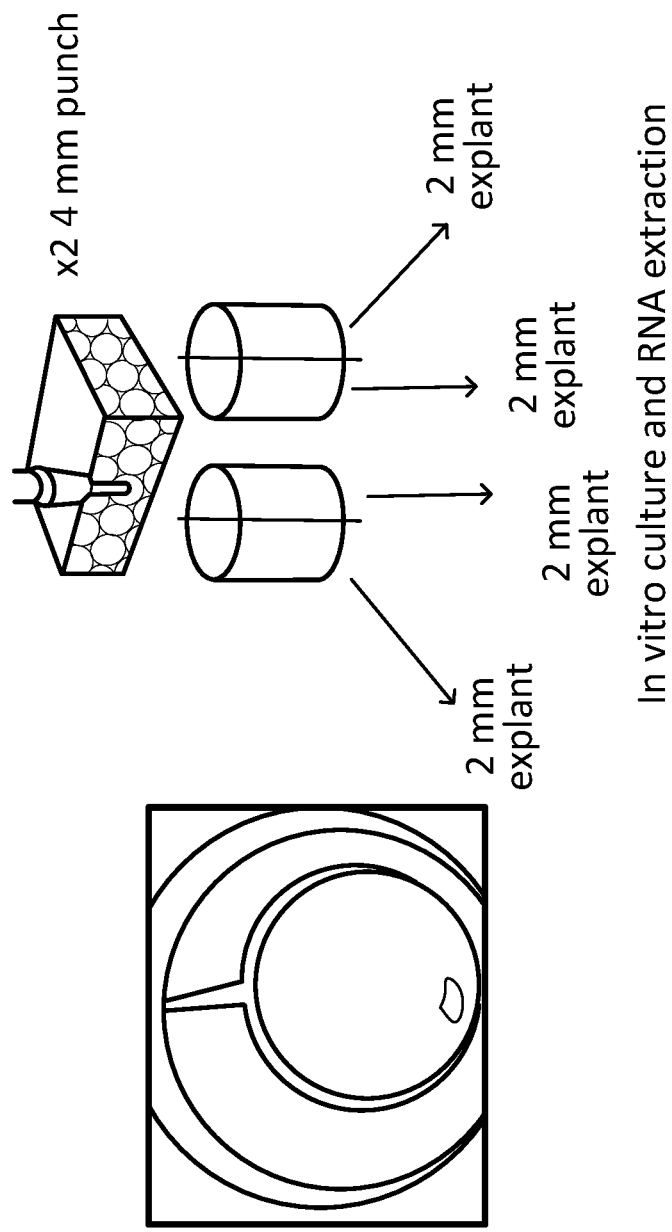
FIG. 1 depicts a representation of skin punch biopsies used for the JAK1 mediated pharmacological inhibition of PN pathophysiology.

Provided herein are methods for the treatment of prurigo nodularis in a subject in need thereof, comprising administering to the subject a therapeutically effective amount of a JAK1 pathway inhibitor, or a pharmaceutically acceptable salt thereof.

Provided herein is a JAK1 pathway inhibitor, or a pharmaceutically acceptable salt thereof, for the treatment of prurigo nodularis in a subject in need thereof.

Provided herein is a use of a JAK1 pathway inhibitor, or a pharmaceutically acceptable salt thereof, for manufacture of a medicament for use in treating prurigo nodularis in a subject in need thereof.

DETAILED DESCRIPTION

The present invention provides, inter alia, a method of treating prurigo nodularis in a subject in need thereof, comprising administering to the subject a therapeutically effective amount of a JAK1 pathway inhibitor, or a pharmaceutically acceptable salt thereof.

In some embodiments, the JAK1 pathway inhibitor, or a pharmaceutically acceptable salt thereof, is selective for JAK1 over JAK2, JAK3, and Tyk2.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (Compound 1), or a pharmaceutically acceptable salt thereof.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

In some embodiments, the JAK1 pathway inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK1 pathway inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

In some embodiments, the JAK1 pathway inhibitor, or a pharmaceutically acceptable salt thereof, is administered in a daily dose of about 5 mg to about 95 mg on a free base basis.

In some embodiments, the JAK1 pathway inhibitor, or a pharmaceutically acceptable salt thereof, is administered in a daily dose of about 15 mg, about 45 mg, about 75 mg, or about 90 mg on a free base basis.

In some embodiments, the JAK1 pathway inhibitor, or pharmaceutically acceptable salt thereof, is administered in a daily dose of about 45 mg or about 75 mg on a free base basis.

In some embodiments, the JAK1 pathway inhibitor, or pharmaceutically acceptable salt thereof, is administered in combination with a further therapeutic agent.

In some embodiments, the further therapeutic agent is a neurokinin 1 receptor antagonist. In some embodiments, the neurokinin 1 receptor antagonist is aprepitant.

In some embodiments, the further therapeutic agent is anti-IL-4/IL-13 antibody. In some embodiments, the anti-IL-4/IL-13 antibody is dupilumab, lebrikizumab or tralokinumab.

In some embodiments, the further therapeutic agent is an anti-IL-5 antibody. In some embodiments, the anti-IL-5 antibody is benralizumab, mepolizumab, or reslizumab.

In some embodiments, the further therapeutic agent is an anti-IL-31 antibody. In some embodiments, the anti-IL-31 antibody is nemolizumab.

In some embodiments, the administering comprises administering the JAK1 pathway inhibitor, or pharmaceutically acceptable salt thereof, together with at least one pharmaceutically acceptable carrier or excipient.

In some embodiments, efficacy of the treatment method disclosed herein can be established based upon an Investigator's Global Assessment (IGA). In some embodiments, the IGA-TS (Investigator's Global Assessment Treatment Success) is defined as an IGA score of 0 or 1 with ≥2 grade improvement from baseline. Efficacy may be established if by evaluating a proportion of subjects achieving an IGA-TS (IGA of 0 or 1 with a 2-point decrease) at a designated point of time (e.g., week 16).

In some embodiments, efficacy of the treatment method disclosed herein can be established based upon Itch Numerical Rating Scale (Itch NRS). In some embodiments, efficacy may be demonstrated by achieving a preset proportion of subjects achieving at least 2 or 4-point improvement in Itch NRS (e.g., at Week 16). In some embodiments, efficacy may be demonstrated by observing time to ≥2-point or ≥4-point improvement from baseline in Itch NRS. In some embodiments, a JAK1 inhibitor (e.g., Compound 1), and/or methods of use described herein result in an improvement in a subject's response to Itch NRS from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to Itch NRS from baseline.

In some embodiments, efficacy of the treatment method disclosed herein can be established based upon Peak Pruritus NRS. The Peak Pruritus Numerical Rating Scale (NRS) was developed to assess one parameter or dimension of itch in clinical trials of drugs in development for patients with moderate-to-severe AD. The Peak Pruritus NRS is a patient-reported outcome test designed to measure peak pruritus, or 'worst' itch, over the previous 24 h. The test is based on, for example, the following question: 'On a scale of 0 to 10, with 0 being "no itch" and 10 being "worst itch imaginable", how would you rate your itch at the worst moment during the previous 24 hours?' In some embodiments, efficacy may be demonstrated by achieving a preset proportion of subjects achieving at least 2 or 4-point improvement in Peak Pruritus NRS (e.g., at Week 16). In some embodiments, efficacy may be demonstrated by observing time to ≥2-point or ≥4-point improvement from baseline in Peak Pruritus NRS. In some embodiments, a JAK1 inhibitor (e.g., Compound 1), and/or methods of use described herein result in an improvement in a subject's response to Peak Pruritus NRS from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to Peak Pruritus NRS from baseline.

In some embodiments, efficacy of the treatment method disclosed herein can be established based upon Nodule Assessment. In some embodiments, a JAK1 inhibitor (e.g., Compound 1), and/or methods of use described herein result in an improvement in a subject's response to PAS from baseline. In some embodiments, a JAK1 inhibitor (e.g., Compound 1), and/or methods of use described herein result in about a 5%, about a 10%, about a 20%, about a 30%, about a 40%, about a 50%, about a 60%, about a 70%, about a 80%, about a 90%, or about a 95% improvement in a subject's response to PAS from baseline. In some embodiments, efficacy of the treatment method disclosed herein can be established based upon photography of effected areas. Photography of the body areas affected with PN will be obtained at visits. All sites will use 2-dimensional photography to photograph areas of the body containing PN nodules.

In some embodiments, efficacy of the treatment method disclosed herein can be established based upon patient-reported outcomes (PROs). In some embodiments, efficacy of the treatment method disclosed herein can be established based upon a Dermatology Life Quality Index (DLQI). In some embodiments, a JAK1 inhibitor (e.g., Compound 1), and/or methods of use described herein result in an improvement in a subject's response to DLQI from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to DLQI from baseline.

In some embodiments, efficacy of the treatment method disclosed herein can be established based upon Patient Global Impression of Change (PGIC). In some embodiments, a JAK1 inhibitor (e.g., Compound 1), and/or methods of use described herein result in an improvement in a subject's response to PGIC from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to PGIC from baseline.

In some embodiments, efficacy can be evaluated based upon improvement in a subject's Hospital Anxiety and Depression Scale (HADS). In some embodiments, a JAK1 inhibitor (e.g., Compound 1), and/or methods of use described herein result in an improvement in a subject's response to HADS from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to HADS from baseline.

In some embodiments, efficacy can be evaluated based upon improvement in a subject's Functional Assessment of Chronic Illness Therapy-Fatigue Scale (FACIT-Fatigue Scale). In some embodiments, a JAK1 inhibitor (e.g., Compound 1), and/or methods of use described herein result in an improvement in a subject's response to FACIT-Fatigue Scale from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to FACIT-Fatigue Scale from baseline.

In some embodiments, efficacy can be evaluated based upon improvement in a subject's PROMIS Sleep Scale. In some embodiments, a JAK1 inhibitor (e.g., Compound 1), and/or methods of use described herein result in an improvement in a subject's response to PROMIS Sleep Scale from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to PROMIS Sleep Scale from baseline.

In some embodiments, efficacy can be evaluated based upon improvement in a subject's EQ-5D-5L questionnaire. In some embodiments, a JAK1 inhibitor, e.g., Compound 1, and/or methods of use described herein result in an improvement in a subject's response to the EQ-5D-5L questionnaire from baseline. In some embodiments, a JAK1 inhibitor, e.g., Compound 1, and/or methods of use described herein result in about a 5%, about a 10%, about a 20%, about a 30%, about a 40%, about a 50%, about a 60%, about a 70%, about a 80%, about a 90%, or about a 95% improvement in a subject's response to EQ-5D-5L from baseline.

The methods described herein utilize JAK1 pathway inhibitors, particularly JAK1 selective inhibitors. A JAK1 selective inhibitor is a compound that inhibits JAK1 activity preferentially over other Janus kinases. JAK1 plays a central role in a number of cytokine and growth factor signaling pathways that, when dysregulated, can result in or contribute to disease states. In autoimmune diseases and cancers, elevated systemic levels of inflammatory cytokines that activate JAK1 may also contribute to the disease and/or associated symptoms. Therefore, patients with autoimmune associated diseases like prurigo nodularis may benefit from JAK1 inhibition. Selective inhibitors of JAK1 may be efficacious while avoiding unnecessary and potentially undesirable effects of inhibiting other JAK kinases. Activated T cells have shown increased IL-22 cytokine expression in patients with PN compared with healthy controls (Belzberg, et al., J Invest Dermatol, 141(9):2208-2218.e14 (2021)).

In some embodiments, the JAK1 pathway inhibitor, or a pharmaceutically acceptable salt thereof, is selective for JAK1 over JAK2, JAK3, and TYK2 (i.e., a JAK1 selective inhibitor). For example, the compounds described herein, or pharmaceutically acceptable salts thereof, preferentially inhibit JAK1 over one or more of JAK2, JAK3, and TYK2. In some embodiments, the compounds inhibit JAK1 preferentially over JAK2 (e.g., have a JAK2/JAK1 $IC_{50}$ ratio >1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP (e.g., see Example A).

In some embodiments, the JAK1 pathway inhibitor is a compound of Table 1, or a pharmaceutically acceptable salt thereof. The compounds in Table 1 are selective JAK1 inhibitors (selective over JAK2, JAK3, and TYK2). The $IC_{50}$ values obtained by the method of Example A at 1 mM ATP are shown in Table 1.

The compounds of Table 1 can be prepared by the synthetic procedures described, for example, in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

TABLE 1

| Comp. No. | Prep. | Name | Structure | JAK1 $IC_{50}$ (nM) | JAK2/JAK1 |
|---|---|---|---|---|---|
| 1 | US 2014/0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 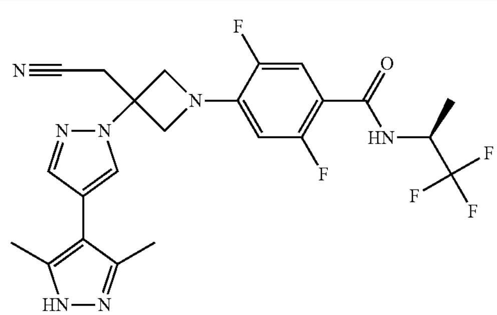 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |

TABLE 1-continued

| Comp. No. | Prep. | Name | Structure | JAK1 IC$_{50}$ (nM) | JAK2/ JAK1 |
|---|---|---|---|---|---|
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 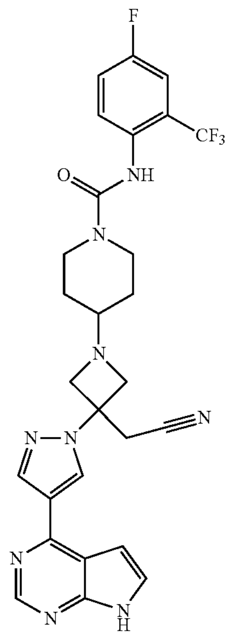 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 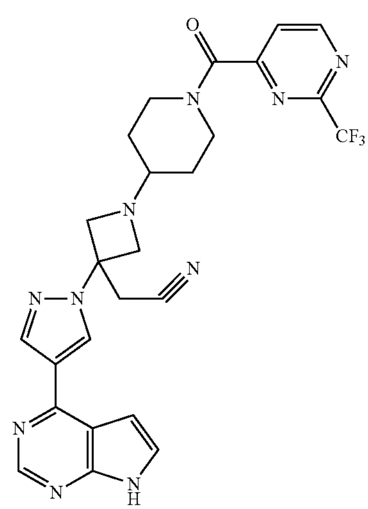 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 4 | US 2011/ 0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 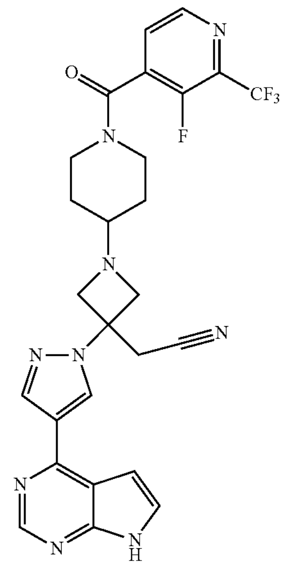 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 5 | US 2014/0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 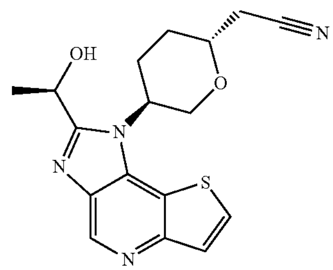 [SMILES: C[C@@H](O)c1nc2cnc3ccsc3c2n1[C@H]1CC[C@H](CC#N)OC1] | ++ | >10 |
| 6 | US 2010/ 0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 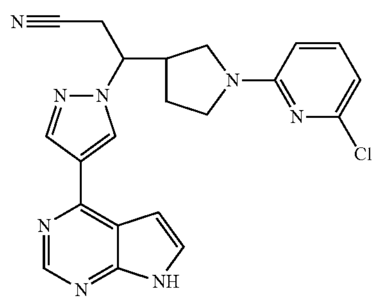 [SMILES: N#CCC(C1CCN(c2cccc(Cl)n2)C1)n1cc(-c2ncnc3[nH]ccc23)cn1] | + | >10 |
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 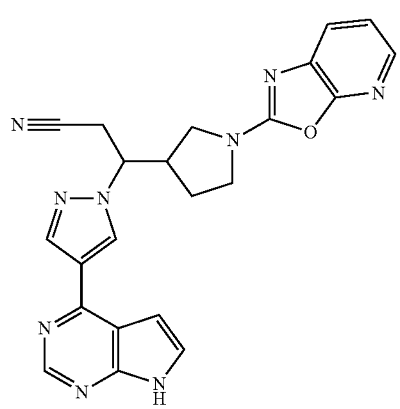 [SMILES: N#CCC(C1CCN(c2nc3cccnc3o2)C1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/ JAK1 |
|---|---|---|---|---|---|
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 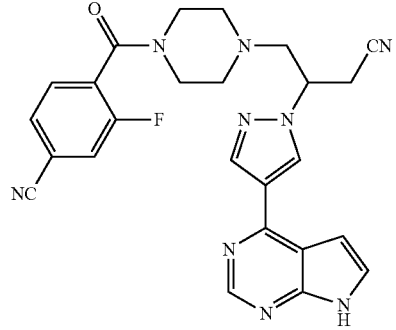 [SMILES: N#CCC(CN1CCN(C(=O)c2ccc(C#N)cc2F)CC1)n1cc(-c2ncnc3[nH]ccc23)cn1] | + | >10 |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 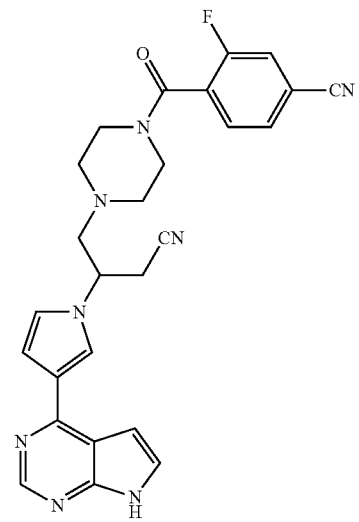 [SMILES: N#CCC(CN1CCN(C(=O)c2ccc(C#N)cc2F)CC1)n1ccc(-c2ncnc3[nH]ccc23)c1] | + | >10 |
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 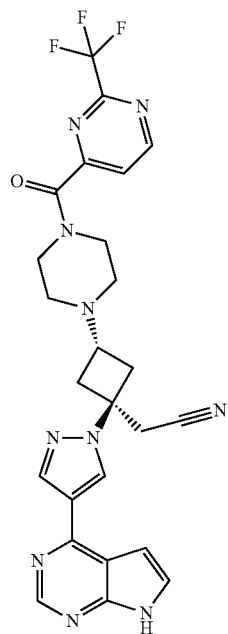 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 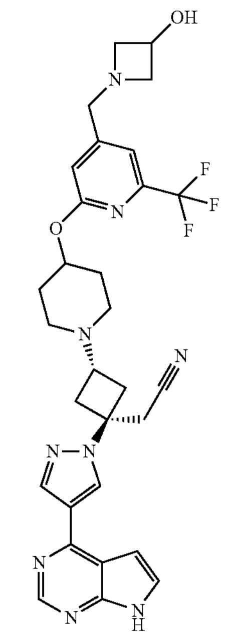 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 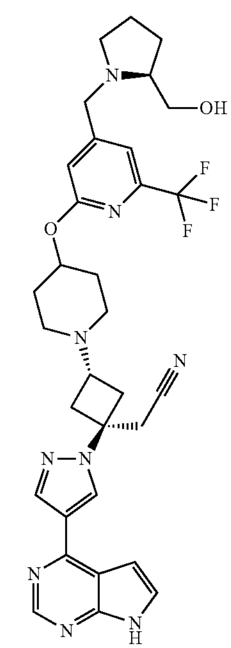 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 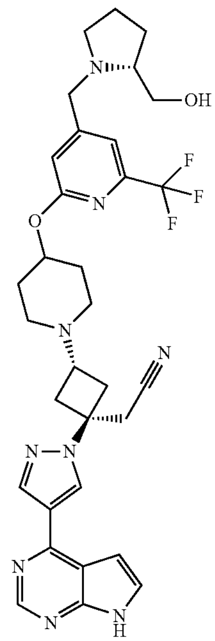 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 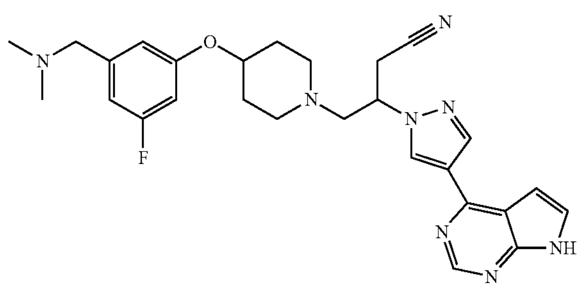 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 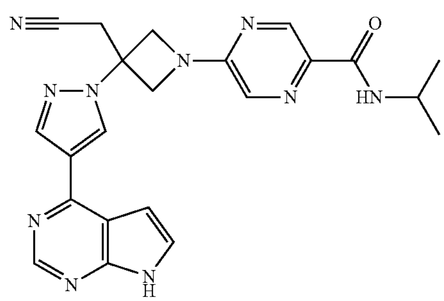 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 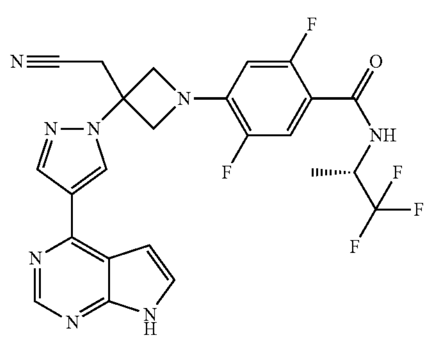 [SMILES: C[C@H](NC(=O)c1cc(F)c(N2CC(CC#N)(n3cc(-c4ncnc5[nH]ccc45)cn3)C2)cc1F)C(F)(F)F] | + | >10 |

TABLE 1-continued

| Comp. No. | Prep. | Name | Structure | JAK1 IC$_{50}$ (nM) | JAK2/JAK1 |
|---|---|---|---|---|---|
| 17 | US 2013/0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 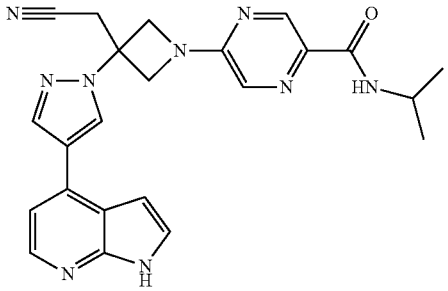 [SMILES: CC(C)NC(=O)c1cnc(N2CC(CC#N)(n3cc(-c4ccnc5[nH]ccc45)cn3)C2)cn1] | + | >10 |
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 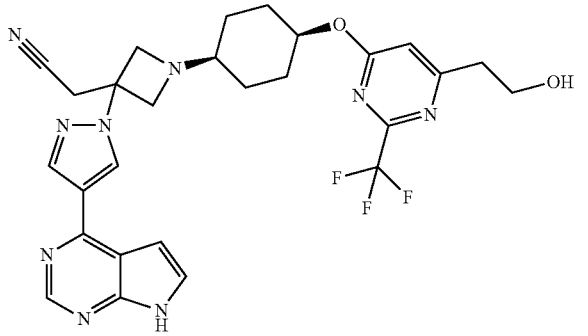 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 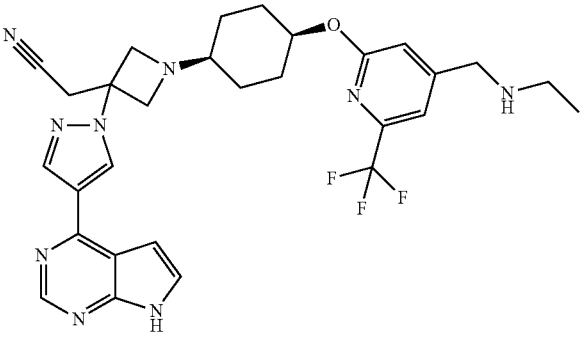 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 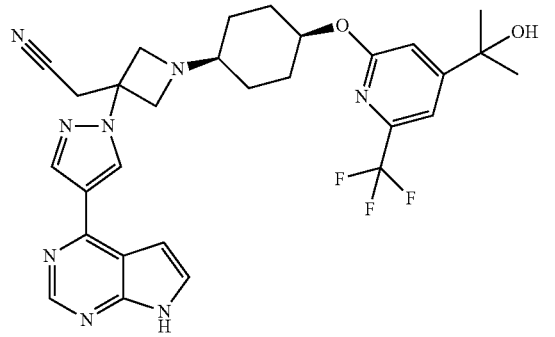 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/JAK1 |
|---|---|---|---|---|---|
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 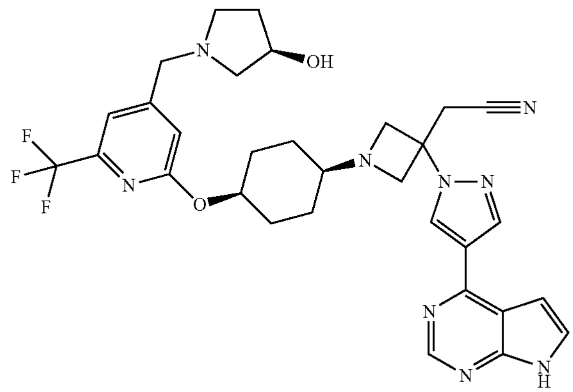 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 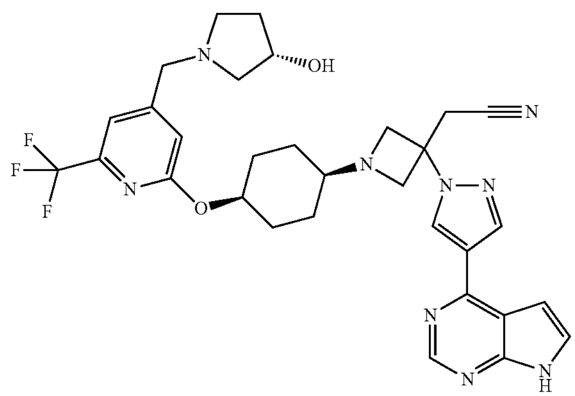 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 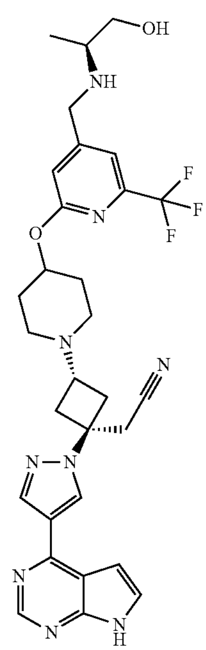 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/JAK1 |
|---|---|---|---|---|---|
| 24 | US 2014/0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 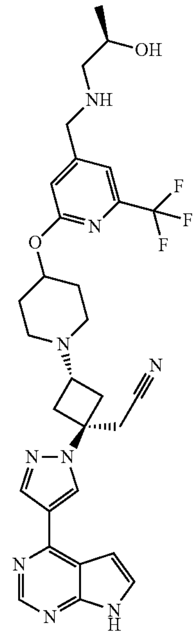 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 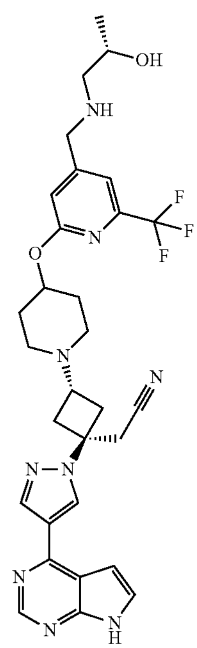 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 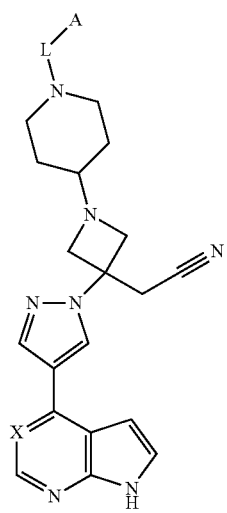 | + | >10 |

+ means <10 nM (see Example A for assay conditions)
++ means ≤100 nM (see Example A for assay conditions)
+++ means ≤300 nM (see Example A for assay conditions)
[a]Data for enantiomer 1
[b]Data for enantiomer 2

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (Compound 1), or a pharmaceutically acceptable salt thereof. In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[1S)-2,2,2-trifluoro-1-methylethyl]benzamide phosphoric acid salt. Compound 1, and its salts, can be made by the procedures described in, e.g., U.S. Pat. No. 9,382,231 (see, e.g., Example 7), filed May 16, 2014, which is incorporated herein by reference in its entirety.

In some embodiments, the JAK1 pathway inhibitor is selected from the compounds, or pharmaceutically acceptable salts thereof, described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. No. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 pathway inhibitor is a compound of Formula I or a pharmaceutically acceptable salt thereof, wherein:
X is N or CH;
L is C(=O) or C(=O)NH;
A is phenyl, pyridinyl, or pyrimidinyl each of which is optionally substituted with 1 or 2 independently selected R$^1$ groups; and
each R$^1$ is, independently, fluoro, or trifluoromethyl.

In some embodiments, the compound of Formula I is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile, or a pharmaceutically acceptable salt thereof.

In some embodiments, the JAK1 pathway inhibitor is a compound of Formula II

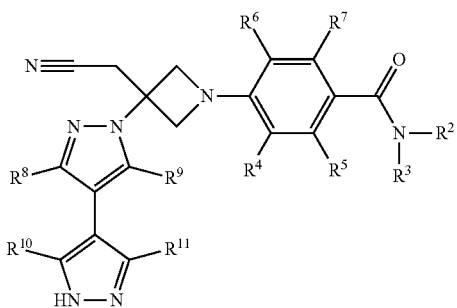

or a pharmaceutically acceptable salt thereof, wherein:
$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;
$R^3$ is H or methyl;
$R^4$ is H, F, or Cl;
$R^5$ is H or F;
$R^6$ is H or F;
$R^7$ is H or F;
$R^8$ is H or methyl;
$R^9$ is H or methyl;
$R^{10}$ is H or methyl; and
$R^{11}$ is H or methyl.

In some embodiments, the JAK1 pathway inhibitor is a compound of Formula III

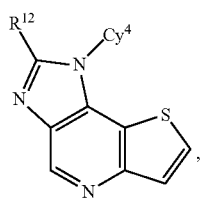

or a pharmaceutically acceptable salt thereof, wherein:
$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and
$R^{12}$ is —$CH_2$—OH, —$CH(CH_3)$—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor, or a pharmaceutically acceptable salt thereof, is administered in a daily amount of from about 10 mg to about 100 mg on a free base basis. Accordingly, in some embodiments, the selective JAK1 pathway inhibitor is administered in a daily amount of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg on a free base basis. In some embodiments, the JAK1 pathway inhibitor, or a pharmaceutically acceptable salt thereof, is administered in a daily amount of from about 1 mg to about 100 mg on a free base basis. In some embodiments, the JAK1 pathway inhibitor, or a pharmaceutically acceptable salt thereof, is administered in a daily amount of from about 10 mg to about 80 mg on a free base basis. In some embodiments, the JAK1 pathway inhibitor, or a pharmaceutically acceptable salt thereof, is administered in a daily amount of about 90 mg on a free base basis. In some embodiments, the JAK1 pathway inhibitor, or a pharmaceutically acceptable salt thereof, is administered in a daily amount of about 75 mg on a free base basis. In some embodiments, the JAK1 pathway inhibitor, or a pharmaceutically acceptable salt thereof, is administered in a daily amount of about 45 mg on a free base basis.

The term "about" means "approximately" (e.g., plus or minus approximately 10% of the indicated value).

In some embodiments, the JAK1 pathway inhibitor, or a pharmaceutically acceptable salt thereof, is administered as one or more sustained release dosage forms each comprising the JAK1 pathway inhibitor, or a pharmaceutically acceptable salt thereof.

In some embodiments, the JAK1 pathway inhibitor, or a pharmaceutically acceptable salt thereof, is administered orally.

The embodiments described herein are intended to be combined in any suitable combination as if the embodiments are multiply dependent claims (e.g., the embodiments related to the selective JAK1 pathway inhibitor and doses of the same, the embodiments related to any salt forms of the compounds disclosed herein, the embodiments related to the individual types of cytokine related diseases or disorders, and the embodiments related to composition and/or administration can be combined in any combination).

All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}B$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 1 can be optionally substituted with deuterium atoms, such as —$CD_3$ being substituted for —$CH_3$). The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

As used herein, the term "subject", "individual," or "patient," used interchangeably, refers to any animal, including mammals, preferably mice, rats, other rodents, rabbits, dogs, cats, swine, cattle, sheep, horses, or primates, and most preferably humans. In some embodiments, the "subject," "individual," or "patient" is in need of said treatment.

In some embodiments, the inhibitors are administered in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the JAK1 inhibitors can prevent prurigo nodularis in an individual who may be predisposed to the disease. The term "preventing" refers to blocking the occurrence of disease in a patient who may be predisposed to the disease but does not yet experience or display the pathology or symptomatology of the disease.

Combination Therapies

The methods described herein can further comprise administering one or more additional therapeutic agents. The one or more additional therapeutic agents can be administered to a patient simultaneously or sequentially. The one or more additional therapeutic agents can be administered using different methods (e.g., topically).

In some embodiments, the additional therapeutic agent is selected from JAK inhibitors. Additional JAK inhibitors may include ATI-50002 (JAK1/3 selective). Additional JAK inhibitors may include PF-06651600 (JAK3 selective). Additional JAK inhibitors may include PF06700841 (JAK1/TYK2 selective). Additional JAK inhibitors may include baricitinib (JAK1/JAK2 selective). Additional JAK inhibitors may include TYK2 selective inhibitors.

In some embodiments, the additional therapeutic agent is selected from antioxidants. Antioxidants may be selected from pseudocatalase, vitamin E, vitamin C, ubiquinone, lipoic acid, *Polypodium leucotomos*, catalase/superoxide dismutase combination, and Ginkgo biloba. In some embodiments, antioxidants may be further administered in combination with phototherapy. The administration of antioxidants during or before phototherapy aims to counteract the oxidative stress induced by UV radiation itself, increasing the phototherapy effectiveness.

In some embodiments, the additional therapeutic agent includes anti-histamines.

In some embodiments, the additional therapeutic agent is an antimetabolite. Antimetabolites may include 5-fluorouracil.

In some embodiments, the additional therapeutic agent is selected from topical corticosteroids, immunomodulators, calcineurin inhibitors, and phototherapy. In some embodiments, the additional therapies are systemic steroids or immunosuppressants.

In some embodiments, the additional therapeutic agent includes steroids (e.g., orally administered steroids) including systemic steroids. Steroid treatment may include oral steroid minipulse therapy (e.g., using betamethasone and/or dexamethasone).

In some embodiments, topical corticosteroids are selected from augmented betamethasone dipropionate, clobetasol propionate, diflorasone diacetate, halobetasol propionate amcinonide, betamethasone valerate, desoximetasone, diflorasone diacetate, fluocinolone acetonide, halcinonide, and triamcinolone acetonide.

In some embodiments, the additional therapeutic agent includes immunomodulators. Immunomodulators may include anti-IL15 therapy (e.g., AMG 714 monoclonal antibody). Immunomodulators may include anti-IL36 therapy (e.g., imsidolimab and spesolimab). Immunomodulators may include anti-TNFalpha therapy (e.g., etanercept and infliximab).

In some embodiments, immunomodulators are selected from apremilast, crisaborole, afamelanotide, minocycline, zinc, tofacitinib, AMG 714 monoclonal antibodies, imsidolimab, spesolimabcyclosporine, etanercept, infliximab, cyclophosphamide, ciclosporin, methotrexate, and sodium oxo-dihydro-acridinylacetate (ODHAA).

In some embodiments, calcineurin inhibitors are selected from tacrolimus (FK-506) and pimecrolimus.

In some embodiments, phototherapy includes exposure to ultraviolet (e.g., excimer lamps or lasers).

In some embodiments, the additional therapeutic agent is a Janus kinase inhibitor. In some embodiments, the Janus kinase inhibitor is administered topically.

In some embodiments, the additional therapeutic agent is a Neurokinin 1 receptor antagonists (e.g., Aprepitant).

In some embodiments, the additional therapeutic agent include anti-IL-4/IL-13 antibodies. In some embodiments, anti-IL-4/IL-13 antibodies are selected from dupilumab, lebrikizumab and tralokinumab.

In some embodiments, the additional therapeutic agent include anti-IL-5 antibodies. In some embodiments, anti-IL-5 antibodies are selected from benralizumab, mepolizumab, and reslizumab.

In some embodiments, the additional therapeutic agent include anti-IL-31 antibodies. In some embodiments, anti-IL-31 antibodies include nemolizumab.

In some embodiments, the additional therapeutic agent is an IL-6 antagonist or receptor antagonist. In some embodiments, the IL-6 receptor antagonist is tocilizumab.

Pharmaceutical Formulations and Dosage Forms

When employed as pharmaceuticals, the JAK1 pathway inhibitors or pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, foams, liquids and powders. Conventional pharmaceutical carriers, aqueous, powder or oily bases, thickeners and the like may be necessary or desirable.

This invention also includes pharmaceutical compositions which contain, as the active ingredient, the JAK1 pathway inhibitor described herein, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The JAK1 pathway inhibitors may be milled using known milling procedures such as wet milling to obtain a particle size appropriate for tablet formation and for other formulation types. Finely divided (nanoparticulate) preparations of the JAK1 selective inhibitors can be prepared by processes known in the art, e.g., see International App. No. WO 2002/000196.

The compositions can be formulated in a unit dosage form, each dosage containing a set amount of the active ingredient as the free form or a salt form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Kits

The present invention also includes pharmaceutical kits useful, for example, in the treatment and/or prevention of prurigo nodularis, which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

Example A: In Vitro JAK Kinase Assay

JAK1 pathway inhibitors that can be used for the treatment of cytokine-related diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2 or JAK3 are assayed by measuring the phosphorylation of a biotinylated peptide. The phosphorylated peptide was detected by homogenous time resolved fluorescence (HTRF). $IC_{50}$s of compounds are measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 μL 45 mM EDTA, 300 nM SA-APC, 6 nM Eu-Py20 in assay buffer (Perkin Elmer, Boston, MA). Binding to the Europium labeled antibody takes place for 40 minutes and HTRF signal was measured on a Fusion plate reader (Perkin Elmer, Boston, MA). The compounds in Table 1 were tested in this assay and shown to have the $IC_{50}$ values also found in Table 1.

Example B

JAK1 Mediated Pharmacological Inhibition of PN Pathophysiology

Full-thickness (4 mm) cutaneous skin biopsies of active disease, untreated, prurigo nodularis were obtained. Two (2) 4-mm punch biopsies were obtained for each lesion (see FIG. 1). The biopsies were longitudinally divided into two pieces for a total of four (4) 2-mm full thickness sections, which were then placed in culture. FIG. 1 depicts a representation of skin punch biopsies used for the JAK1 mediated pharmacological inhibition of PN pathophysiology. Biopsies were then cultured in the presence of a vehicle control (DMSO) or small molecule JAK1 inhibitor compound (in this particular case Compound 1) for 8 days. Every 2 days the supernatant was collected for cytokine/protein analysis. Collected supernatants were analyzed to quantify chemokines, cytokines, and growth factors secreted by skin explants in culture. A total of 51 proteins were detected and quantified in culture supernatants by Procarta Multiplex Immunoassay (Thermo Fisher, Waltham, MA). Supernatants and standards were incubated at 4° C. overnight. Assay plates were read on a Luminex 200 Instrument (Luminex Corporation, Austin, TX). The concentration was extrapolated from the antigen standard curve of each analyte. The percent inhibition was determined for each analyte as the difference in protein concentration in cultures with DMSO ($C_D$) versus those with the JAK1 inhibitor, Compound 1 ($C_J$), or ($C_D$-$C_J$)/CD, See FIG. 2.

Figure 2:
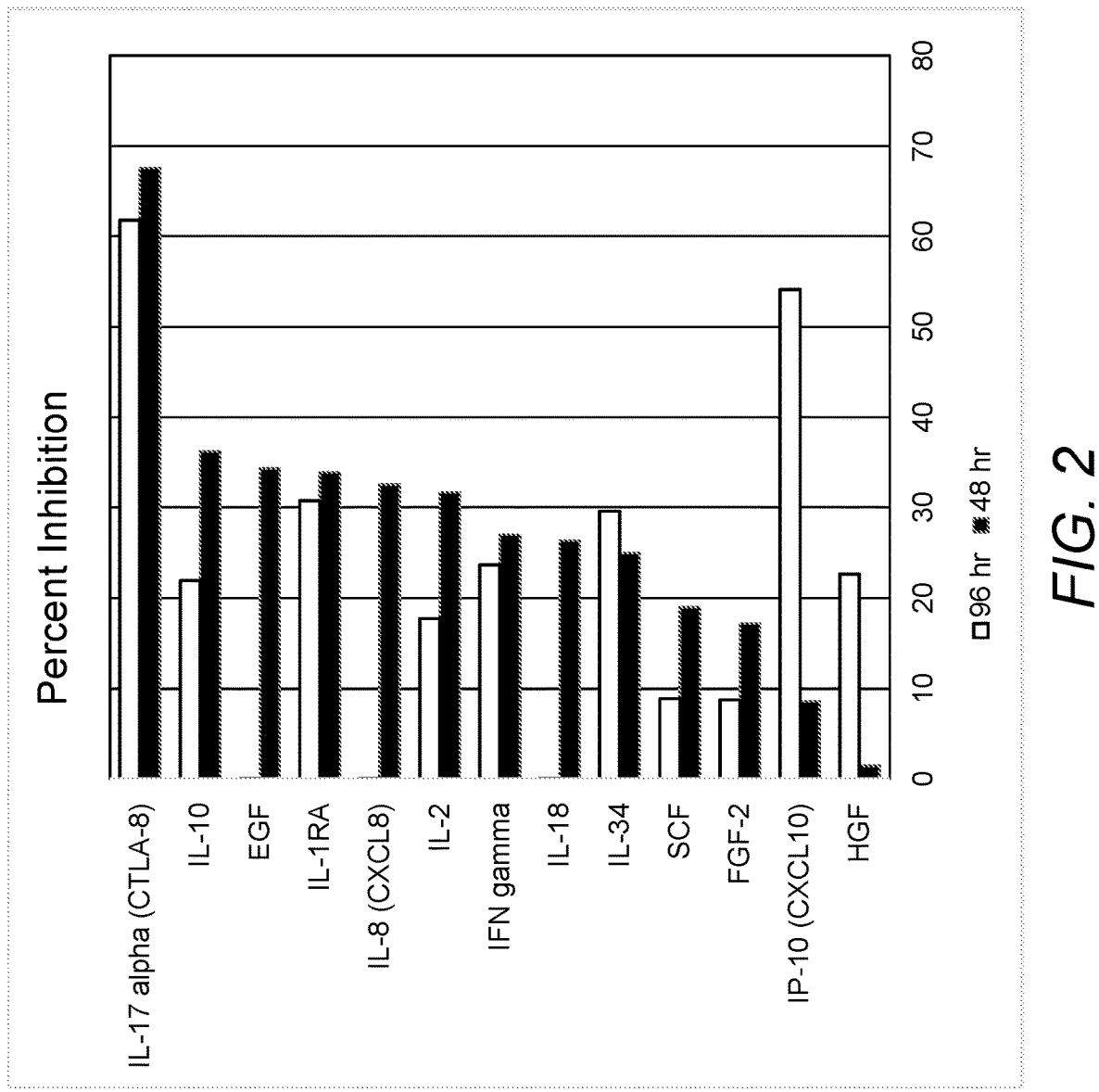
FIG. 2 depicts a graphical representation of JAK1 mediated pharmacological inhibition of PN pathophysiology using JAK1 inhibitor Compound 1.

Compound 1 was shown to inhibit key chemokines, cytokines, and growth factors involved in key disease pathways (see Table 2 and FIG. 2). These key chemokines, cytokines, and growth factors are involved in inflammation, pruritus (itching), or lesion development that can be associated with PN. For example, PN lesional skin has been shown to have increased levels of CXCL8, CXCL10, and interferon-gamma when compared to non-lesional control skin (Tsoi et al., J Allergy Clin Immunol 149, 1329-39 (2022)).

Further, other cytokines, such as IL-31 and IL-17, have also been shown to play a role in PN. For example, CD4+ T-cells has been shown to significantly infiltrate lesional PN skin as compared to non-lesional control skin (Wong, et al., J Investigative Dermatology, 140(3), 702-706.e2 (2020)). CD4+ T-cells can express interleukin 31 (IL-31), which has been shown to be a mediator of pruritus—an important symptom of PN (Ständer, et al., N Engl J Med, 382:706-716 (2020)). The expressed IL-31 has also been shown to play a role in the development of PN with inhibition of IL-31 by nemolizumab resulting in improvement in pruritus and skin lesions in PN patients (Ständer, supra). When PN skin was cultured nemolizumab (an IL-31 inhibitor), a reduction in IL-17 levels in lesional skin was observed, suggesting that inhibiting IL31R signaling can impact IL-17 expression (Tsoi, supra). Further, cells expressing IL-17 are increased in the dermis of PN lesional skin as compared to control skin (Wong, supra). Further, IL-2 is critical to the development, maintenance and function of the infiltrating CD4+ T-cells (Furtado, J Exp Med, 196(6):851-7 (2002)) and is a strong itch mediator (Xie, et al., J Dermatol, 46(3), 177-185 2019)). Further, the epidermis of PN skin has been shown to be positive for STAT6, a marker for Th2 cytokines, such as IL-5 and IL-31 (Mullins, et al., NLM, StatPearls Publishing, https://www.ncbi.nlm.nih.gov/books/NBK459204), Sep. 14, 2021)). Finally, keratinocytes are implicated in the pathogenesis of PN, particularly around pruritus (Zhong et al, Acta Dermato-Venereologicavolume 99, 579-5861 May (2019)). In skin, keratinocytes produce IL-34.

Hence, Compound 1 has been shown to inhibit multiple key chemokines, cytokines, and growth factors involved in PN and/or the underlying inflammation and pruritus associated with PN.

TABLE 2 showing percent inhibition due to Compound 1

| | | |
|---|---|---|
| HGF | 1.46 | 22.65 |
| IP-10 (CXCL10) | 8.53 | 54.12 |
| IL-22 | 11.16 | ** |
| VEGF-A | 16.92 | 7.79 |
| FGF-2 | 17.17 | 8.70 |
| SCF | 18.98 | 8.85 |
| IL-5 | 20.25 | ** |
| IL-34 | 24.98 | 29.61 |
| IL-18 | 26.35 | ** |
| IFN GAMMA | 26.98 | 23.67 |
| IL-2 | 31.63 | 17.75 |
| IL-8 (CXCL8) | 32.51 | 4.38 |
| IL-1RA | 33.82 | 30.75 |
| EGF | 34.30 | ** |
| IL-10 | 36.18 | 21.91 |
| IL-17 ALPHA (CTLA-8) | 67.51 | 61.79 |

** no measureable inhibition

Example C: Phase 2 Study of Compound 1

Study Design

Figure 3:
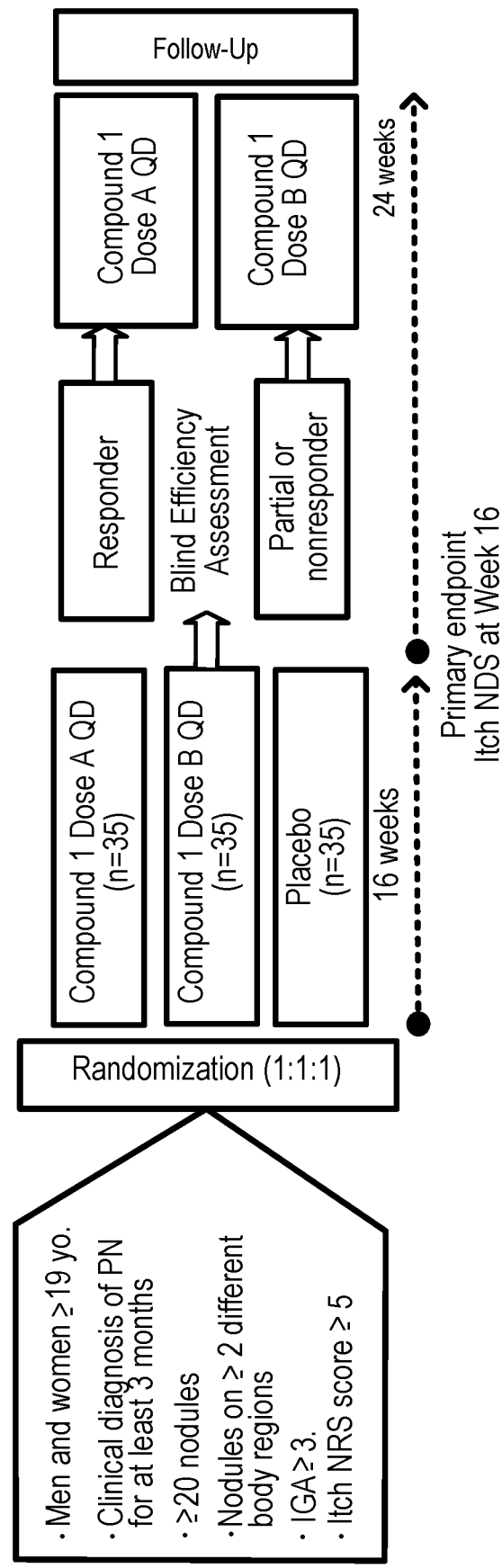
FIG. 3 depicts an outline of a phase 2 randomized, double-blind, placebo-controlled dose-ranging study of the efficacy and safety of Compound 1.

A phase 2 randomized, double-blind, placebo-controlled dose-ranging study of the efficacy and safety of JAK inhibitor Compound 1 treatment of prurigo nodularis patients is described. FIG. 3 depicts the study conducted using Compound 1 for treating participants with prurigo nodularis. The study can include a 24-week double-blind extension period in participants with prurigo nodularis. Participants can include those with prurigo nodularis (e.g., clinically diagnosed for at least 3 months) who have a total of ≥20 nodules, nodules on ≥2 different body regions, an IGA ≥3, and severe pruritus. The study can include men and women of at least 18 years of age.

Participants will participate for up to 48 weeks, including up to 4 weeks for screening, up to 40 weeks for treatment (16 weeks in the placebo-controlled period and 24 weeks in the extension), and 4 weeks for safety follow-up. Approximately 105 participants will be randomized 1:1:1 to 1 of 3 treatment groups (Dose A (45 mg (e.g., 3 Compound 1 15 mg tablets and 2 placebo tablets)), Dose B (75 mg (e.g., 5 Compound 1 15 mg tablets)), or placebo (e.g., 5 placebo tablets)). Compound 1 or matching placebo will be taken orally QD. Based on the efficacy response at Week 16, participants will receive 1 of the 2 doses of active study drug for an additional 24 weeks. For example, someone is a responder if responsive to treatment by achieving ≥4-point decrease in Itch NRS (based on weekly average itch score) and IGA-TS (score of 0 or 1 with ≥2 grade improvement from baseline) and not responsive if they do not meeting the definition of a responder.

In some embodiments, criteria for participants to be included in the study include any one of the following: men and women ≥18 years of age or above; clinical diagnosis of prurigo nodularis for at least 3 months; ≥20 nodules; nodules on ≥2 different body regions; IGA ≥3; and severe pruritus. Severe pruritus may be defined by: an average Itch NRS score ≥5 for the week preceding screening; and an average Itch NRS ≥5 for the week before Day 1 (note: participants must have at least 4 of 7 days of itch data before baseline to calculate an average and be randomized). Participants must be willing to take appropriate, medically acceptable, contraceptive measures to avoid pregnancy or fathering a child for the duration of study participation. Also, female participants must have a negative serum pregnancy test at screening and a negative urine pregnancy test before randomization on Day 1.

Embodiments of the schedules of activities for the placebo-controlled and extension periods are presented in Table 3 and Table 4, respectively.

TABLE 3

| | | | Placebo-Controlled Treatment | | | | | | Safety Follow-up | Notes Week 16 assessments must be complete before participant can continue in the study. |
|---|---|---|---|---|---|---|---|---|---|---|
| Visit Day (Range) | Screening Days −28 to −1 | Day 1 (Baseline) | Week 2 (remote) (±3 d) | Week 4 (±3 d) | Week 6 (remote) (±3 d) | Week 8 (±3 d) | Week 12 (±3 d) | Week 16/ET (±3 d) | (+7 d) after last dose | |
| Administrative procedures | | | | | | | | | | |
| Informed consent | X | | | | | | | | | |
| I/E criteria review | X | X | | | | | | | | |
| Demography and medical history | X | | | | | | | | | General and disease-specific medical history. |
| Prior/concomitant medications | X | X | X | X | X | X | X | X | X | |
| Contact IRT | X | X | | X | | X | X | X | | |
| Randomization | | X | | | | | | | X* | * Possible change in dose based on efficacy assessment. |
| Distribute reminder card and diaries | | X | | X | | X | X | X | | |
| Study drug taken at visit | | | | | | | | | | |

TABLE 3-continued

| Visit Day (Range) | Screening Days −28 to −1 | Day 1 (Baseline) | Placebo-Controlled Treatment | | | | | | Safety Follow-up 28 days (+7 d) after last dose | Notes Week 16 assessments must be complete before participant can continue in the study. |
| --- | --- | --- | --- | --- | --- | --- | --- | --- | --- | --- |
| | | | Week 2 (remote) (±3 d) | Week 4 (±3 d) | Week 6 (remote) (±3 d) | Week 8 (±3 d) | Week 12 (±3 d) | Week 16/ET (±3 d) | | |
| Dispense study drug | | X | | X | | X | X | X | | |
| Collect study drug and review diary cards | | X | | X | | X | X | X | | |
| Assess e-diary compliance | | X | | X | | X | X | X | | |
| Assess study drug compliance | | X | | X | | X | X | X | | |
| Safety assessments | | | | | | | | | | |
| AE assessments | X | X | X | X | X | X | X | X | X | If an AE is noted, that body systems should be physically examined. |
| Comprehensive physical examination | X | | | | | | | X* | | *Comprehensive physical examination only if ET visit. |
| Height | X | | | | | | | | | |
| Body weight | X | | | | | | | X | | |
| Vital signs | X | X | | X | | X | X | X | X | |
| 12-lead ECG | X | | | | | | | X | | |
| Efficacy assessments | | | | | | | | | | |
| IGA | X | X | | X | | X | X | X | X | |
| Nodule assessment | X | X | | X | | X | X | X | X | |
| Itch NRS | | Diary is completed each evening from screening through the dose of study drug. | | | | | | | | |
| Photography | | X | | | | X | | X | X | |
| Quality of life assessments Note: Should be conducted before any other assessments. | | | | | | | | | | |
| DLQI | X | X | | X | | X | X | X | X | |
| EQ-5D | X | X | | X | | X | X | X | X | |
| PGIC | | | | X | | X | X | X | X | |
| HADS | X | X | | X | | X | X | X | X | |
| FACIT Fatigue | X | X | | X | | X | X | X | X | |
| PROMIS Sleep | X | X | | X | | X | X | X | X | |
| Laboratory assessments Note: Blood draw for clinical laboratory tests must be performed before study drug is taken in-clinic, as appropriate. | | | | | | | | | | |
| Chemistry assessments | X | X* | X | X | X | X | X | X | X | *Not necessary if screening assessment performed within 14 days of Day 1. |
| Hematology assessments | X | X* | X | X | X | X | X | X | X | |
| Pregnancy testing | X | X | | X | | X | X | X | X | *WOCBP will have a serum test at screening and follow-up and a urine test at all other in-clinic visits. A positive urine test must be confirmed by a serum test. |
| Coagulation | X | | | | | X | | X | | |
| Urinalysis | X | | | | | X | | X | | |
| TB screening | X | | | | | | | | | |
| Serology | X | | | | | | | | | |
| Thyroid function | X | | | | | | | | | |
| Inflammation marker | | X | | | | X | | X | | |
| PK blood draw | | | | X | | | X | | | Visits TBD |
| Skin biopsy | | | | | | | | | | Visits TBD |

TABLE 4

| Visit Day (Range) | Extension Treatment | | | | | | | Safety Follow-up 28 days | Notes |
|---|---|---|---|---|---|---|---|---|---|
| | Week 18 (remote) (±3 d) | Week 20 (±3 d) | Week 22 (remote) (±3 d) | Week 24 (±3 d) | Week 28 (±3 d) | Week 32 (±3 d) | Week 36 (±3 d) | Week 40/ET (±3 d) | (+7 d) after last dose |
| Administrative procedures | | | | | | | | | |
| Prior/concomitant medications | X | X | X | X | X | X | X | X | X | |
| Contact IRT | | X | | X | X | X | X | X | | |
| Distribute reminder cards | | X | | X | X | X | X | X | | |
| Study drug taken at visit | | | | | | | | | | |
| Dispense study drug | | X | | X | X | X | X | | | |
| Collect study drug and review diaries | | X | | X | X | X | X | X | | |
| Assess e-diary compliance | | X | | X | X | X | X | X | | |
| Assess study drug compliance | | X | | X | X | X | X | X | | |
| Safety assessments | | | | | | | | | | |
| AE assessments | X | X | X | X | X | X | X | X | X | If an AE is noted, that body systems should be physically examined. |
| Comprehensive physical examination | | | | | | | | X | | |
| Body weight | | | | | X | | | X | | |
| Vital signs | | X | | X | X | X | X | X | X | |
| 12-lead ECG | | | | | | | | X | | |
| Efficacy assessments | | | | | | | | | | |
| IGA | | X | | X | X | X | X | X | X | |
| Itch NRS | Diary is completed each evening from screening through the dose of study drug. | | | | | | | | | |
| Nodule assessment | | X | | X | X | X | X | X | X | |
| Photography | | | | | | | | | | Maybe not at all in the ext. |
| Quality of life assessments Note: Should be conducted before any other assessments. | | | | | | | | | | |
| DLQI | | X | | X | X | X | X | X | X | |
| EQ-5D-5L | | X | | X | X | X | X | X | X | |
| PGIC | | X | | X | X | X | X | X | X | |
| HADS | | X | | X | X | X | X | X | X | |
| FACIT-Fatigue | | X | | X | X | X | X | X | X | |
| PROMIS Sleep | | X | | X | X | X | X | X | X | |
| Laboratory assessments Note: Blood draw for clinical laboratory tests must be performed before study drug is taken in-clinic, as appropriate. | | | | | | | | | | |
| Chemistry | X | X | X | X | X | X | X | X | X | |
| Hematology | X | X | X | X | X | X | X | X | X | |
| Pregnancy | | X | | X | X | X | X | X | | *WOCBP: serum test at screening and follow-up and urine test at all other in-clinic visits. Positive urine test must be confirmed by a serum test. |
| Coagulation | | | | X | | | | X | | |
| Urinalysis | | | | X | | | | X | | |
| Thyroid function | | | | | | | | | | |
| Inflammation marker | | | | X | | | | X | | |
| Pharmacokinetics | | | | X | | | | | | Visits TBD |

In some embodiments, criteria for participants to be excluded from the study include any one of the following: chronic pruritus due to a condition other than prurigo nodularis (e.g., such as scabies, insect bite, lichen simplex chronicus, psoriasis, acne, folliculitis, habitual picking, lymphomatoid papulosis, chronic actinic dermatitis, dermatitis herpetiformis, sporotrichosis, bullous disease, excoriation syndrome); neuropathic and psychogenic pruritus (e.g., notalgia paresthetica, brachioradial pruritus, small fiber neuropathy, skin picking syndrome, or delusional parasitosis); and concurrent conditions and history of other diseases. Concurrent conditions and history of other diseases can include: thrombocytopenia, coagulopathy, platelet dysfunction, or history of thrombotic events; immunocompromised (e.g., lymphoma, acquired immunodeficiency syndrome, Wiskott-Aldrich Syndrome) or have a history of malignant disease within 5 years before baseline; chronic or acute infection requiring treatment with systemic antibiotics, antivirals, antiparasitics, antiprotozoals, or antifungals within 2 weeks before the baseline visit; active acute bacterial, fungal, or viral skin infection (e.g., herpes simplex, herpes zoster, chicken pox, clinically infected atopic dermatitis, impetigo) within 1 week before the baseline visit; any other concomitant skin disorder (e.g., generalized erythroderma such as Netherton's Syndrome), pigmentation, or extensive scarring that in the opinion of the investigator may interfere with the evaluation of PN lesions or assessments of efficacy or compromise participant safety; current herpes zoster infection, a history of disseminated herpes simplex, or a history of herpes zoster; history of malignancy, including melanoma, lymphoma, and leukemia within 5 years before Day 1, other than a successfully treated nonmetastatic cutaneous squamous cell carcinoma, basal cell carcinoma, or localized carcinoma in situ of the cervix; and albinism.

In some embodiments, criteria for participants to be excluded any of the following treatments within an indicated washout period before the baseline visit: current use of anticoagulants or medications known to cause thrombocytopenia; 4 weeks—systemic corticosteroids or adrenocorticotropic hormone analogs, cyclosporin, methotrexate, azathioprine, or other systemic immunosuppressive or immunomodulating agents (e.g., mycophenolate or tacrolimus) (note: use of corticosteroid inhalers and intranasal sprays is allowed and use of oral corticosteroids for non-dermatologic conditions (e.g., asthma exacerbation, bronchitis) is allowed for no longer than 7 days, if deemed acceptable by the investigator and the sponsor); 2 weeks—systemic antibiotics and immunizations; sedating antihistamines unless on long-term stable regimen (nonsedating antihistamines are permitted) (note: live vaccine are not recommended during the course of the study); 1 week—use of any topical treatments for PN (other than bland emollients), such as corticosteroids, calcineurin inhibitors, PDE4 inhibitors, coal tar (shampoo), topical antibiotics, antibacterial cleansing body wash/soap (unless on long-term stable regimen); <12 weeks or 5 half-lives (if known), whichever is longer, for any topical or systemic JAK or TYK2 inhibitor; <12 weeks or 5 half-lives (if known), whichever is longer, for any investigational or experimental treatments; <12 weeks or 5 half-lives (if known), whichever is longer, for systemic immunosuppressive or immunomodulating biologic drugs; <6 weeks for live vaccine, or planning to receive live vaccine during the course of the study or within 6 weeks after the last dose of study drug; <3 weeks for any oral or topical PDE-4 inhibitor (e.g., apremilast, crisaborole); <2 weeks or 5 half-lives (if known), whichever is longer, for strong and moderate systemic CYP3A4 inhibitors and strong systemic CYP3A4 inducers; and <1 week for antiplatelet drugs, note: Low-dose acetylsalicylic acid (≤100 mg QD) is permitted for the purpose of cardiovascular prophylaxis at the discretion of the investigator.

In some embodiments, criteria for participants to be excluded from the study include uncontrolled thyroid function at screening as determined by the investigator (note: if the participant has a history of thyroid disease and is on treatment, the participant must be on a stable thyroid regimen for at least 3 months prior to Day 1). In some embodiments, criteria for participants to be excluded from the study include laboratory values at screening defined in Table 5.

TABLE 5

| | Laboratory Parameter | Exclusion Criterion |
|---|---|---|
| | Hematology | |
| a | Platelets | $<150 \times 10^9$/L |
| b | Hemoglobin | $<10$ g/L |
| c | ANC | $<1.5 \times 10^9$/L |
| d | WBC | $\leq 3.0 \times 10^9$/L |
| | Hepatic | |
| e | ALT | $\geq 2 \times$ ULN |
| f | AST | $\geq 2 \times$ ULN |
| g | Conjugated (direct) bilirubin/total bilirubin | $\geq 1.2 \times$ ULN/$\geq 1.5 \times$ ULN (Note: unless clinical diagnosis of Gilbert's syndrome) |
| h | Alkaline phosphatase | $\geq 2 \times$ ULN |
| | Renal | |
| j | eGFR | $\leq 70$ mL/minute based on Cockcroft-Gault formula |
| | Coagulation | |
| l | PT | >ULN |
| m | INR | >ULN |

In some embodiments, criteria for participants to be excluded from the study include evidence of HBV or HCV infection or risk of reactivation. Participants cannot be positive for hepatitis B surface antigen, anti-hepatitis B core antibody, or HCV antibody; participants also cannot be positive for HBV DNA or HCV RNA in case these reflexive assessments are required to be performed (participants with no prior history of HBV infection who have been vaccinated against HBV and who have a positive antibody (hepatitis B surface antibody) against HBsAg as the only evidence of prior exposure may participate in the study; and participants with a history of HCV infection who are antibody positive and have been successfully treated >12 weeks ago, and have no detectable HCV RNA, are allowed in the study). In some embodiments, criteria for participants to be excluded from the study include known HIV infection.

In some embodiments, criteria for participants to be excluded from the study include evidence of active or latent or inadequately treated infection with *Mycobacterium tuberculosis* (i.e., TB) as defined by the following: a positive QFT-GIT or positive Mantoux/PPD tuberculin skin test performed at or within the 12 weeks prior to Day 1 is exclusionary; a history of either untreated or inadequately treated latent or active TB infection; if a participant has previously received an adequate course of therapy for either latent TB infection or active TB infection, neither a QFT-GIT nor a Mantoux/PPD tuberculin skin test is needed, but a chest x-ray(s) or other appropriate diagnostic image, performed within 3 months of Day 1, is required; and a participant who is currently being treated for active TB infection is to be excluded.

In some embodiments, criteria for participants to be excluded from the study include known hypersensitivity or severe reaction to Compound 1 or excipients of Compound 1. In some embodiments, criteria for participants to be excluded from the study include pregnant or lactating participants, or those considering pregnancy. In some embodiments, criteria for participants to be excluded from the study include history of alcoholism or drug addiction within 1 year before screening or current alcohol or drug use that, in the opinion of the investigator, will interfere with the participant's ability to comply with the administration schedule and study assessments. In some embodiments, criteria for participants to be excluded from the study include inability or unlikeliness of the participant to comply with the dose schedule and study evaluations, in the opinion of the investigator.

In some embodiments, efficacy of the treatment method disclosed herein can be established based upon an Investigator's Global Assessment (IGA). The IGA is The IGA is an overall severity rating on a 0 to 4 as noted in Table 6. In some embodiments, the IGA-TS (Investigator's Global Assessment Treatment Success) is defined as an IGA score of 0 or 1 with ≥2 grade improvement from baseline. Efficacy may be established if by evaluating a proportion of participants achieving an IGA-TS (IGA of 0 or 1 with a 2-point decrease) at a designated point of time (e.g., week 16).

TABLE 6

| Grade | Severity | Status |
|---|---|---|
| 0 | Clear | No nodules (0 nodules) |
| 1 | Almost clear | Rare, flattened lesions, with no more than 5 dome-shaped palpable nodules (approximately 1-5 nodules) |
| 2 | Mild | Few, mostly flattened lesions, with small number of dome-shaped palpable nodules (approximately 6-19 nodules) |
| 3 | Moderate | Many lesions, partially flattened, and dome-shaped palpable nodules (approximately 20-100 nodules) |
| 4 | Severe | Abundant lesions, majority are dome-shaped palpable nodules (over 100 nodules) |

In some embodiments, efficacy of the treatment method disclosed herein can be established based upon Itch Numerical Rating Scale (Itch NRS). Participants may be issued a hand-held device (eDiary) for daily assessments. The participant can be instructed to complete the diary during specific timepoints needed for each assessment beginning on the day of screening through a set endpoint (e.g., Week 40) or treatment discontinuation. In some embodiments, efficacy may be demonstrated by achieving a preset proportion of participants achieving at least 2 or 4-point improvement in Itch NRS (e.g., at Week 16). In some embodiments, efficacy may be demonstrated by observing time to ≥2-point or ≥4-point improvement from baseline in Itch NRS. In some embodiments, Compound 1 and/or methods of use described herein result in an improvement in a participant's response to NRS from baseline.

In some embodiments, efficacy of the treatment method disclosed herein can be established based upon Nodule Assessment. In some embodiments, the number of nodules will be counted at each in-clinic visit and disease activity will be assessed via the PAS. In some embodiments, Compound 1 and/or methods of use described herein result in an improvement in a participant's response to PAS from baseline. PAS (Prurigo Activity Score) will assess disease activity in terms of percentage of pruriginous lesions with excoriations/crusts on top (reflecting active scratching) and the percentage of healed pruriginous lesions is measured by the subitem "Activity" of PAS in order to quantify change of Prurigo nodularis skin lesions.

In some embodiments, efficacy of the treatment method disclosed herein can be established based upon photography of effected areas. Photography of the body areas affected with PN will be obtained at visits. All sites will use 2-dimensional photography to photograph areas of the body containing PN nodules.

In some embodiments, efficacy of the treatment method disclosed herein can be established based upon patient-reported outcomes (PROs). In some embodiments, efficacy of the treatment method disclosed herein can be established based upon a Dermatology Life Quality Index (DLQI). In some embodiments, Compound 1 and/or methods of use described herein result in an improvement in a participant's response to DLQI from baseline. The DLQI is a validated questionnaire (e.g., 10-question) to measure how much the skin problem has affected the participant over the previous 7 days as outlined in the SoAs. The participant will answer the questionnaire with either (1) very much, (2) a lot, (3) a little, or (4) not at all. The questionnaire can be analyzed under 6 headings: symptoms and feelings; daily activities; leisure; work and school; personal relations; and treatment.

In some embodiments, efficacy of the treatment method disclosed herein can be established based upon Patient Global Impression of Change (PGIC). In some embodiments, Compound 1 and/or methods of use described herein result in an improvement in a participant's response to PGIC from baseline. The PGIC is a participants' self-reporting measure that reflects their belief about the efficacy of treatment. The PGIC is a 7-point scale depicting a participant's rating of overall improvement and will be captured during site visits. For example, the participant will answer the following: "Since the start of the treatment you've received in this study, your PN in areas treated with the study drug is: (1) very much improved, (2) much improved, (3) minimally improved, (4) no change, (5) minimally worse, (6) much worse, and (7) very much worse."

In some embodiments, efficacy can be evaluated based upon improvement in a participant's Hospital Anxiety and Depression Scale (HADS). In some embodiments, Compound 1 and/or methods of use described herein result in an improvement in a participant's response to HADS from baseline. HADS is 14-item questionnaire that assesses the levels of anxiety and depression that a person is currently experiencing. There are 7 questions each for measuring anxiety and for measuring depression, with 4 possible responses to each question (responses are scored as 0, 1, 2, or 3). Separate scores are calculated for anxiety and depression.

In some embodiments, efficacy can be evaluated based upon improvement in a participant's Functional Assessment of Chronic Illness Therapy-Fatigue Scale (FACIT-Fatigue Scale). In some embodiments, Compound 1 and/or methods of use described herein result in an improvement in a participant's response to FACIT-Fatigue Scale from baseline. The FACIT-Fatigue scale is validated instrument, with a 13-item questionnaire originally designed to assess fatigue in patients with chronic disease as a 7-day recall period. Each item uses a 5-point scale ranging from "4=not at all" to "0=very much." The total FACIT-Fatigue score ranges from 0 (maximum fatigue) to 52 (no fatigue). The participant should complete the questionnaire before site personnel perform any clinic assessments and before any interaction with the site personnel has occurred to avoid biasing the participant's response.

In some embodiments, efficacy can be evaluated based upon improvement in a participant's PROMIS Sleep Scale. In some embodiments, Compound 1, and/or methods of use described herein result in an improvement in a participant's response to PROMIS Sleep Scale from baseline. With the PROMIS Sleep Scale sleep will be assessed using 2 of the PROMIS: Short Forms, Sleep-Related Impairment and Sleep-Disturbance. The PROMIS Short Form—Sleep-Related Impairment questionnaire assesses self-reported perceptions of alertness, sleepiness, and tiredness during usual waking hours and the perceived functional impairments during wakefulness associated with sleep problems or impaired alertness. The questionnaire has 8 questions, which are assessed using a 5-point scale. Scores range from 8 to 40, with higher scores indicating greater severity of sleep-related impairment. The PROMIS Short Form—Sleep Disturbance questionnaire assesses self-reported perceptions of sleep quality, sleep depth, and restoration associated with sleep. Sleep disturbance does not focus on symptoms of specific sleep disorders and does not provide subjective estimates of sleep quantities (e.g., total amount of sleep, time to fall asleep, amount of wakefulness during sleep). The sleep disturbance short form is generic rather than disease-specific. The questionnaire had 8 questions and is assessed using a 5-point scale. Scores range from 8 to 40, with higher scores indicating greater severity of sleep disturbance.

In some embodiments, efficacy can be evaluated based upon improvement in a participant's EQ-5D-5L questionnaire. In some embodiments, Compound 1, and/or methods of use described herein result in an improvement in a participant's response to the EQ-5D-5L questionnaire from baseline. The EQ-5D-5L questionnaire is a standardized, validated instrument for use as a measure of health outcome. The EQ-5D-5L questionnaire will provide data for use in economic models and analyses, including developing health utilities or Quality-Adjusted Life Years (QALYs). The EQ-5D-5L questionnaire consists of the following 2 sections: the EQ-5D descriptive system and the EQ VAS. The descriptive system comprises five dimensions: mobility, self-care, usual activities, pain/discomfort, and anxiety/depression.

Each dimension has 5 levels: Level 1 is "no problems," Level 2 is "slight problems," Level 3 is "moderate problems," Level 4 is "severe problems," and Level 5 is "extreme problems." This part of the EQ-5D-5L questionnaire provides a descriptive profile that can be used to generate a health state profile. For example, a participant in "health state 12345" would have no problems with mobility, slight problems with self-care (washing or dressing), moderate problems with doing usual activities, severe pain or discomfort and extreme anxiety or depression. Each health state can potentially be assigned a summary index score based on societal preference weights for the health state. These weights, sometimes referred to as utilities, are often used to compute QALYs for use in health economic analyses. Health state index scores generally range from less than 0 (where 0 is the value of a health state equivalent to dead; negative values representing values as worse than dead) to 1 (the value of full health), with higher scores indicating higher health utility. The health state preferences often represent national or regional values and can therefore differ between countries/regions. The EQ VAS records the participant's self-rated health on a vertical visual analogue scale (0 to 100), where the endpoints are labelled "the best health you can imagine" (100 score) and "the worst health you can imagine" (0 score).

Several populations will be analyzed. In some embodiments, an intent-to-treat (ITT) will be analyzed. The ITT population includes all randomized participants. Treatment groups for this population will be defined according to the treatment assignment at randomization. In some embodiments, a safety population will be analyzed. The safety population includes all participants who received at least 1 dose of study drug, Treatment groups for this population will be determined according to the actual treatment the participant received on Day 1. In some embodiments, a PK/PD evaluable population will be analyzed. The PK/PD evaluable population includes participants who received at least 1 dose of study drug (Compound 1 and/or placebo) and provided at least 1 postdose PK/PD sample/assessment. The study pharmacokineticist will review data listings of participant administration and sample records to identify participants to be excluded from the analysis.

Statistical Analyses

In some embodiments, a primary analysis will be based on the ITT population. The primary alternative hypothesis (superiority of Compound 1 groups compared with placebo group for proportion of participants achieving 4-point improvement in Itch NRS at Week 16 (responders)) will be tested using exact logistic regression. This model will include the treatment groups and stratification factors. The unadjusted p-values between each of Compound 1 groups versus placebo group will be compared with the pre-specified the significance level. Odds ratio and corresponding 95% confidence interval will be provided as well. All nonresponders in the placebo-controlled period, as well as all participants who are missing post-baseline values, will be defined as nonresponders for the nonresponder imputation analysis.

In some embodiments, a secondary efficacy analyses will be conducted on the ITT population. All secondary efficacy variables will be summarized using descriptive statistics. For the binary endpoint, proportion of participants achieving an IGA-TS (IGA of 0 or 1 with a 2-point decrease) at Week 16, summary statistics will include sample size, frequency, and percentages. For the time-to-event endpoint, time to ≥2-point improvement from baseline in Itch NRS, Kaplan-Meier curves will be presented by treatment groups. The number of participants, number of events and number of censoring will be summarized by treatment groups. The KM estimate of median time will be presented with its 95% CI.

In some embodiments, a safety analyses will be conducted on the safety population. A TEAE is any AE either reported for the first time or worsening of a pre-existing event after first dose of study drug up to 28 days after the last dose of study drug. Analysis of AEs will be limited to TEAEs, but data listings will include all AEs regardless of their timing to study drug administration. Adverse events will be tabulated by the MedDRA preferred term and system organ class. Severity of AEs will be based on the National Cancer Institute CTCAE v5.0 using Grades 1 through 5.

The subset of AEs considered by the investigator to have a relationship to study drug will be considered to be treatment-related AEs. If the investigator does not specify the relationship of the AE to study drug, then the AE will be considered treatment-related. The incidence of AEs and treatment-related AEs will be tabulated.

The clinical laboratory data will be analyzed using summary statistics; no formal treatment group comparisons are planned. Laboratory test values outside the normal range will be assessed for severity based on the normal ranges for the clinical reference laboratory. The incidence of abnormal laboratory values and shift tables relative to baseline will be tabulated. Descriptive statistics and mean change from baseline will be determined for vital signs (blood pressure, pulse, respiratory rate, and body temperature) at each assessment time. Descriptive statistics and mean change from baseline will be determined for each ECG parameters at each assessment time.

In some embodiments, all exploratory efficacy variables will be summarized using descriptive statistics. For categorical measurements, summary statistics will include sample size, frequency, and percentages. For continuous measurements, summary statistics will include sample size, mean, median, standard deviation, minimum, and maximum. Summary statistics for continuous measures will be provided for baseline, the actual measurements at each visit, and the change and percentage change from baseline at each visit, if applicable. For the time-to-event endpoint, the number of participants, number of events and number of censoring will be summarized by treatment groups. The KM estimate of median time will be presented with its 95% CI.

In some embodiments, pharmacokinetic analyses will be performed in the PK evaluable population. The Compound 1 plasma concentration data will be analyzed by a population PK modeling approach. Such data may be combined with data from other studies in the clinical development program to develop or refine population PK models, in which populations of healthy participants, hidradenitis suppurativa participants and/or vitiligo participants will be evaluated, and included into the model if significant, as a covariate. This model may be used to evaluate the effects of intrinsic and extrinsic covariates on the PK of Compound 1 and to determine measures of individual plasma exposures (such as steady-state peak, trough, and/or time-averaged concentrations). A data analysis plan and results of population PK analysis will be reported separately.

In some embodiments, pharmacokinetic/pharmacodynamic analysis will be explored in the PK/PD evaluable population. Clinical response such as platelet count, etc, will be analyzed. A data analysis plan and results of population PK/PD analysis will be reported separately.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method for treating prurigo nodularis in a subject, said method comprising administering to the subject a therapeutically effective amount of JAK1 pathway inhibitor 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof, to a subject in need thereof.

2. The method of claim 1, wherein the JAK1 pathway inhibitor is a pharmaceutically acceptable salt of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide.

3. The method of claim 1, wherein the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

4. The method of claim 1, wherein the JAK1 pathway inhibitor, or pharmaceutically acceptable salt thereof, is administered in a daily dose of about 5 mg to about 95 mg on a free base basis.

5. The method of claim 1, wherein the JAK1 pathway inhibitor, or pharmaceutically acceptable salt thereof, is administered in a daily dose of about 45 mg or about 75 mg on a free base basis.

6. The method of claim 1, wherein the JAK1 pathway inhibitor, or pharmaceutically acceptable salt thereof, is administered in combination with a further therapeutic agent.

7. The method of claim 6, wherein the further therapeutic agent is a neurokinin 1 receptor antagonist.

8. The method of claim 7, wherein the neurokinin 1 receptor antagonist is aprepitant.

9. The method of claim 6, wherein the further therapeutic agent is anti-IL-4 and/or anti-IL-13 antibody.

10. The method of claim 9, wherein the anti-IL-4 and/or anti-IL-13 antibody is dupilumab, lebrikizumab or tralokinumab.

11. The method of claim 6, wherein the further therapeutic agent is an anti-IL-5 antibody.

12. The method of claim 11, wherein the anti-IL-5 antibody is benralizumab, mepolizumab, or reslizumab.

13. The method of claim 6, wherein the further therapeutic agent is an anti-IL-31 antibody.

14. The method of claim 13, wherein the anti-IL-31 antibody is nemolizumab.

15. The method of claim 1, wherein the administering comprises administering the JAK1 pathway inhibitor, or pharmaceutically acceptable salt thereof, together with at least one pharmaceutically acceptable carrier or excipient.

16. The method of claim 1, wherein the JAK1 pathway inhibitor, or pharmaceutically acceptable salt thereof, is administered in a daily dose of about 10 mg to about 80 mg on a free base basis.

17. The method of claim 1, wherein the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide.

18. The method of claim 1, wherein the JAK1 pathway inhibitor, or pharmaceutically acceptable salt thereof, is administered in a daily dose of about 45 mg to about 75 mg on a free base basis.

19. The method of claim 1, wherein the JAK1 pathway inhibitor, or pharmaceutically acceptable salt thereof, is administered in a daily dose of about 45 mg on a free base basis.

20. The method of claim 1, wherein the JAK1 pathway inhibitor, or pharmaceutically acceptable salt thereof, is administered in a daily dose of about 75 mg on a free base basis.

* * * * *